United States Patent
Xu et al.

(10) Patent No.: US 11,697,813 B2
(45) Date of Patent: Jul. 11, 2023

(54) PHARMACEUTICAL COMPOSITIONS AND METHODS OF USE FOR ACTIVATION OF HUMAN FIBROBLAST AND MYOFIBROBLAST APOPTOSIS

(71) Applicants: Sirnaomics, Inc., Gaithersburg, MD (US); Jia Zhou, Gaithersburg, MD (US); Qingfeng Li, Gaithersburg, MD (US)

(72) Inventors: John Xu, Germantown, MD (US); Patrick Y. Lu, Potomac, MD (US); Jia Zhou, Gaithersburg, MD (US); Qingfeng Li, Shanghai (CN); Vera Simonenko, Gaithersburg, MD (US)

(73) Assignees: Sirnaomics, Inc., Germantown, MD (US); Sirnaomics Medicine Technology (Suzhou) Co, Ltd., Suzhou (CN)

(*) Notice: Subject to any disclaimer, the term of this patent is extended or adjusted under 35 U.S.C. 154(b) by 824 days.

(21) Appl. No.: 16/343,309

(22) PCT Filed: Oct. 30, 2017

(86) PCT No.: PCT/US2017/059072
§ 371 (c)(1),
(2) Date: Apr. 18, 2019

(87) PCT Pub. No.: WO2018/081726
PCT Pub. Date: May 3, 2018

(65) Prior Publication Data
US 2020/0392507 A1 Dec. 17, 2020

Related U.S. Application Data

(60) Provisional application No. 62/414,780, filed on Oct. 30, 2016.

(51) Int. Cl.
| | | |
|---|---|---|
| C07H 21/02 | (2006.01) | |
| C07H 21/04 | (2006.01) | |
| C12N 15/113 | (2010.01) | |
| A61K 31/713 | (2006.01) | |
| A61K 47/34 | (2017.01) | |

(52) U.S. Cl.
CPC ........ *C12N 15/1136* (2013.01); *A61K 31/713* (2013.01); *A61K 47/34* (2013.01); *C12N 15/1137* (2013.01); *C12N 2310/14* (2013.01); *C12N 2320/30* (2013.01)

(58) Field of Classification Search
CPC .......................... C12N 15/113; C12N 2310/14
See application file for complete search history.

(56) References Cited

U.S. PATENT DOCUMENTS

| | | |
|---|---|---|
| 2013/0225655 A1 | 8/2013 | Lu et al. |
| 2014/0072613 A1 | 3/2014 | Lander et al. |
| 2015/0065431 A1* | 3/2015 | Xu .................... A61K 31/5415 514/420 |

FOREIGN PATENT DOCUMENTS

| | | |
|---|---|---|
| CN | 103642800 A | 3/2014 |
| CN | 104174032 A | 12/2014 |
| WO | 2011/140285 A2 | 11/2011 |

OTHER PUBLICATIONS

Santiago et al. (The Journal of Investigative Dermatology, 125, 450-455, 2005).*
Bertrand et al. (Biochemical and Biophysical Research Communications, 296, 2002, 1000-1004).*
Leng et al. (Cancer Gene Therapy, 2008, 15, 485-495).*
Coward et al. (Molecular and Cellular Biology, 2009, 4325-4339).*
Elbashir et al. (The EMBO Journal, vol. 20, No. 23, pp. 6877-6888, 2001).*
International Search Report and the Written Opinion in PCT/US2017/059072, dated Apr. 26, 2018, 13 pages.
European Search Report in corresponding EP Application No. 17865833.2, dated Aug. 4, 2020, 22 pages.
Anonymous "NCT02956317 v2: A Randomized, Double-Blind, Within-Subject Placebo Controlled Study to Evaluate the Safety and Efficacy of Various Doses of STP705 Administered as Intradermal Injection in Subjects With Hypertrophic Scar", Retrieved from the Internet: URL:https://clinicaltrials.gov/ct2/history/NCT02956317?V_2=View#StudyPageTop, 2016, 8 pages.
Anonymous "Sirnaomics Initiates a Clinical Phase IIa Study of Its Leading siRNA Therapeutic Candidate, STP705, for Treatment of Hypertrophic Scar", Retrieved from the Internet: URL:https://www.prnewswire.com/news-releases/sirnaomics-initiates-a-clinical-phase-iia-study-of-its-leading-sirna-therapeutic-candidate-stp705-for-treatment-of-hypertrophic-scar-300402392.html, 2017, 3 pages.

* cited by examiner

*Primary Examiner* — Amy H Bowman
(74) *Attorney, Agent, or Firm* — Edell, Shapiro & Finnan, LLC

(57) ABSTRACT

The current invention provides a method of activating fibroblast and myofibroblast apoptosis in a tissue of a mammal, comprising administering to the tissue a therapeutically effective amount of a composition comprising an siRNA molecule that binds to an mRNA that codes for TGFB1 protein in a mammalian cell, an siRNA molecule that binds to an mRNA that codes for COX-2 protein in a mammalian cell, and a pharmaceutically acceptable carrier comprising a pharmaceutically acceptable histidine-lysine polymer. The invention also provides additional methods for using this composition.

11 Claims, 23 Drawing Sheets

Specification includes a Sequence Listing.

|        | TGF-β1                              | COX-2                              |
|--------|-------------------------------------|-------------------------------------|
| siRNA  | 5'-CCCAAGGGCUACCAUGCCAACUUCU-3'     | 5'-GGUCUGGUGCCUGGUCUGAUGAUGU-3'    |
| Human  | 5'-CCCAAGGGCUACCAUGCCAACUUCU-3'     | 5'-GGUCUGGUGCCUGGUCUGAUGAUGU-3'    |
| Mouse  | 5'-CCCAAGGGCUACCAUGCCAACUUCU-3'     | 5'-GGUCUGGUGCCUGGUCUGAUGAUGU-3'    |
| Monkey | 5'-CCCAAGGGCUACCAUGCCAACUUCU-3'     | 5'-GGUCUGGUGCCUGGUCUGAUGAUGU-3'    |
| Pig    | 5'-CCCAAGGGCUACCAUGCCAAuUUCU-3' | 5'-GGUCUGGUGCCUGGUCUGAUGAUGU-3'    |

Figure 1. Selected siRNA Oligos with Homology to Human, Mouse, Monkey and pig corresponding genes.

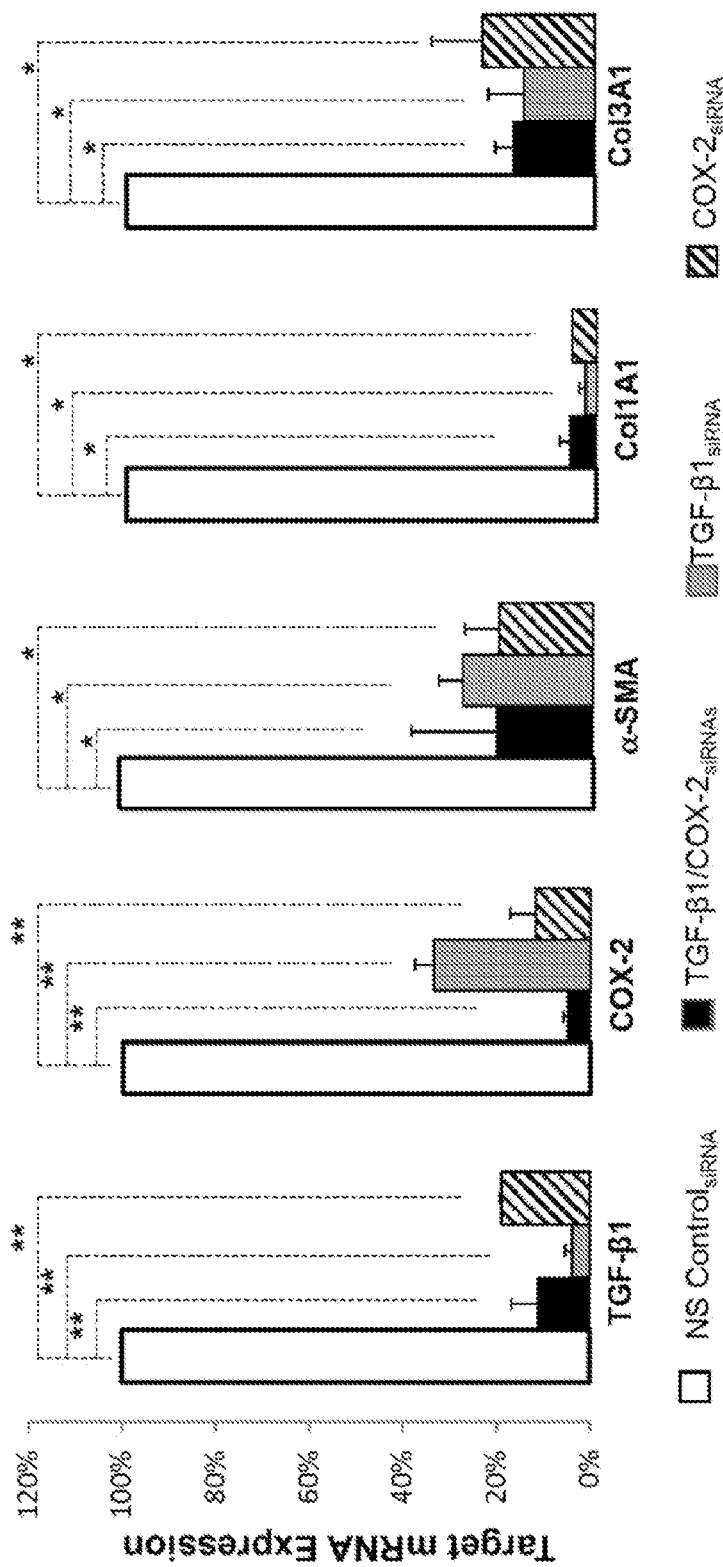
Figure 2. Comparisons of target gene silencing effects

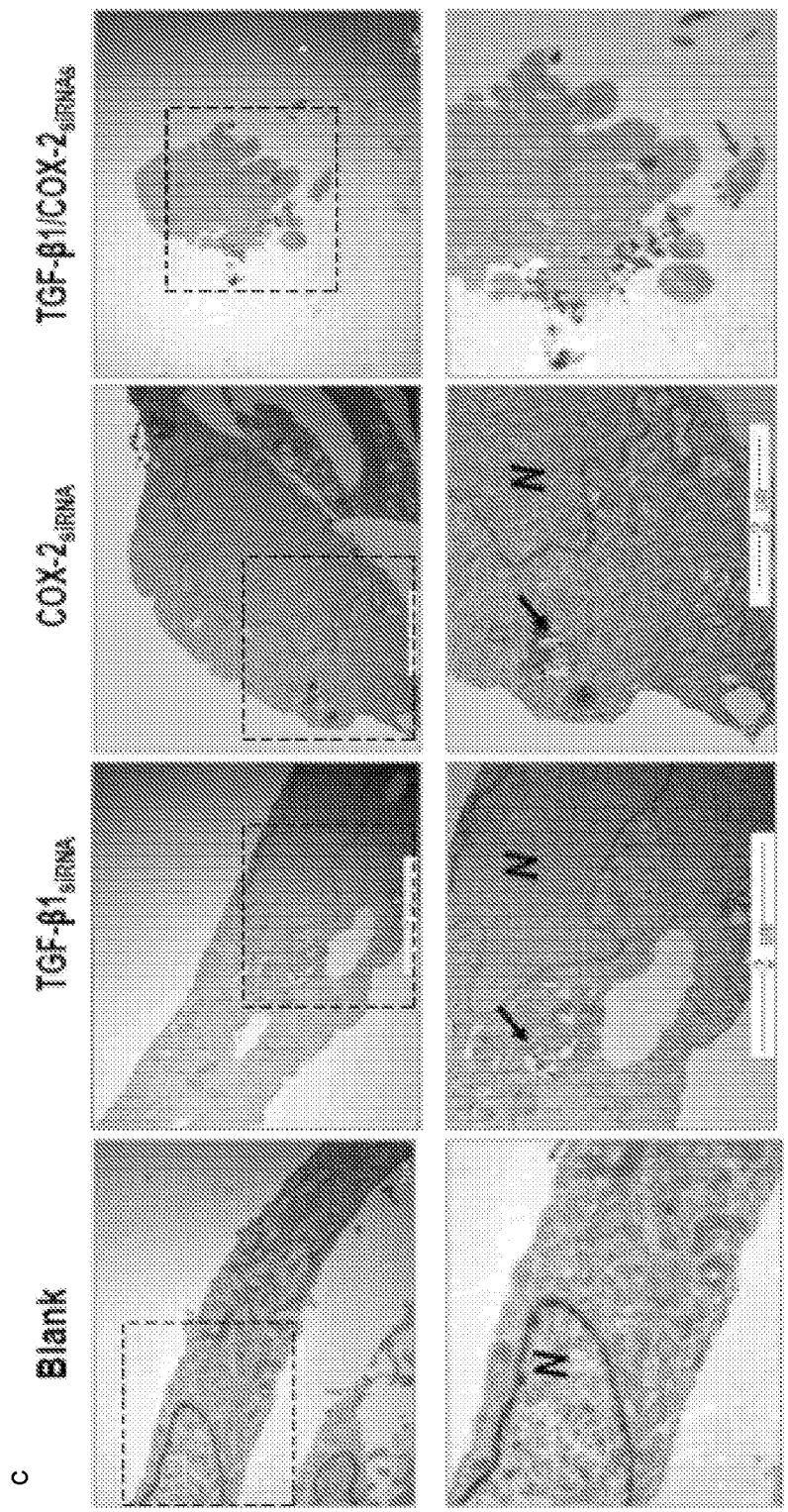
Figure 3. Electron Microscopic (TEM) observation of siRNA entry and myofibroblast apoptosis

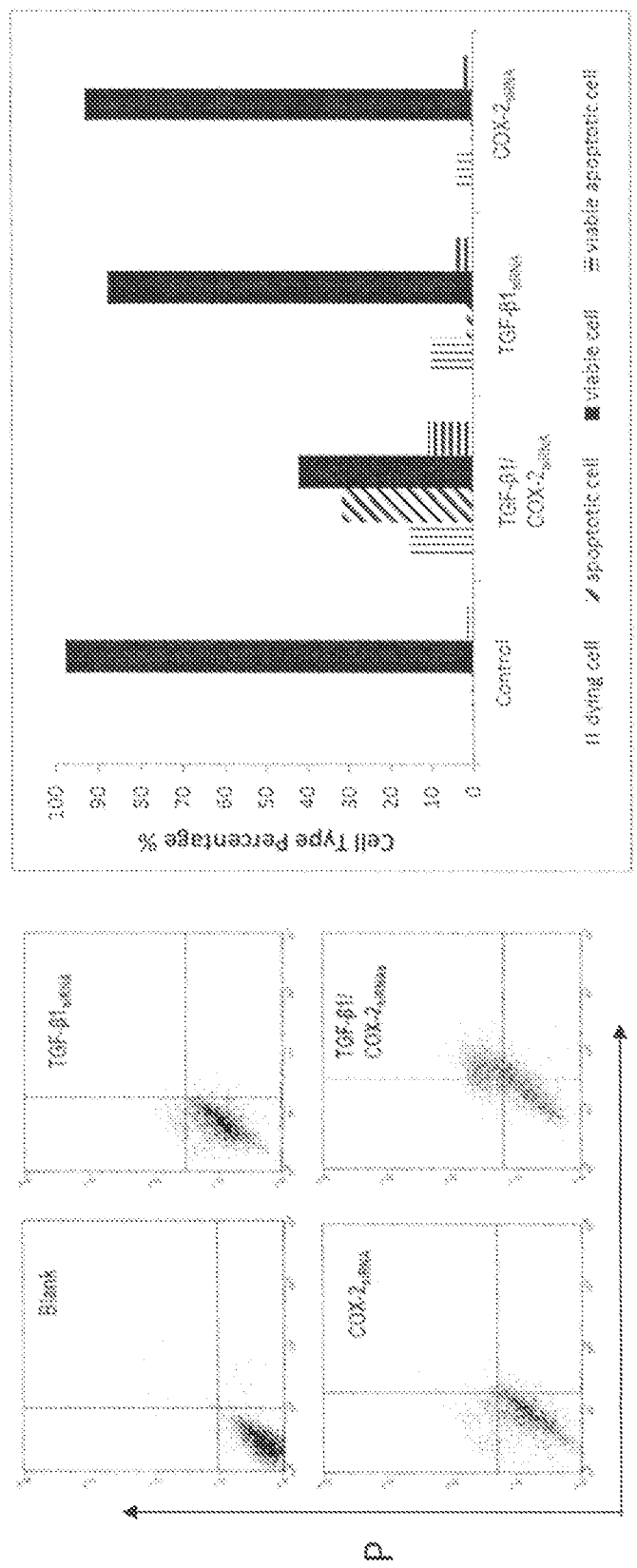
Figure 4. Comparisons of apoptotic activities (left) and quantification of the apoptotic activities (right) of treated myofibroblas isolated from human hypertrophic scars.

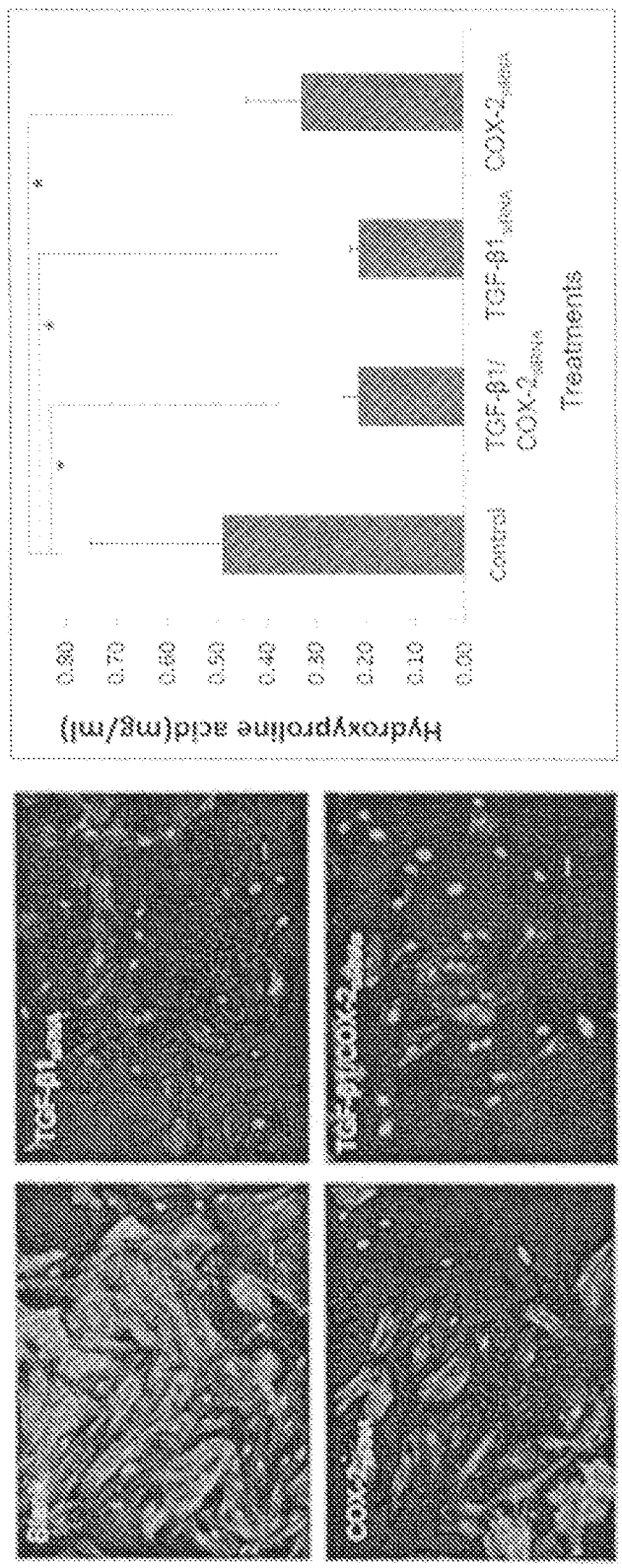
Figure 5. Comparisons of α-SMA expressions (left) and hydroxproline acid levels (right) of the treated myofibroblas isolated from human hypertrophic scars.

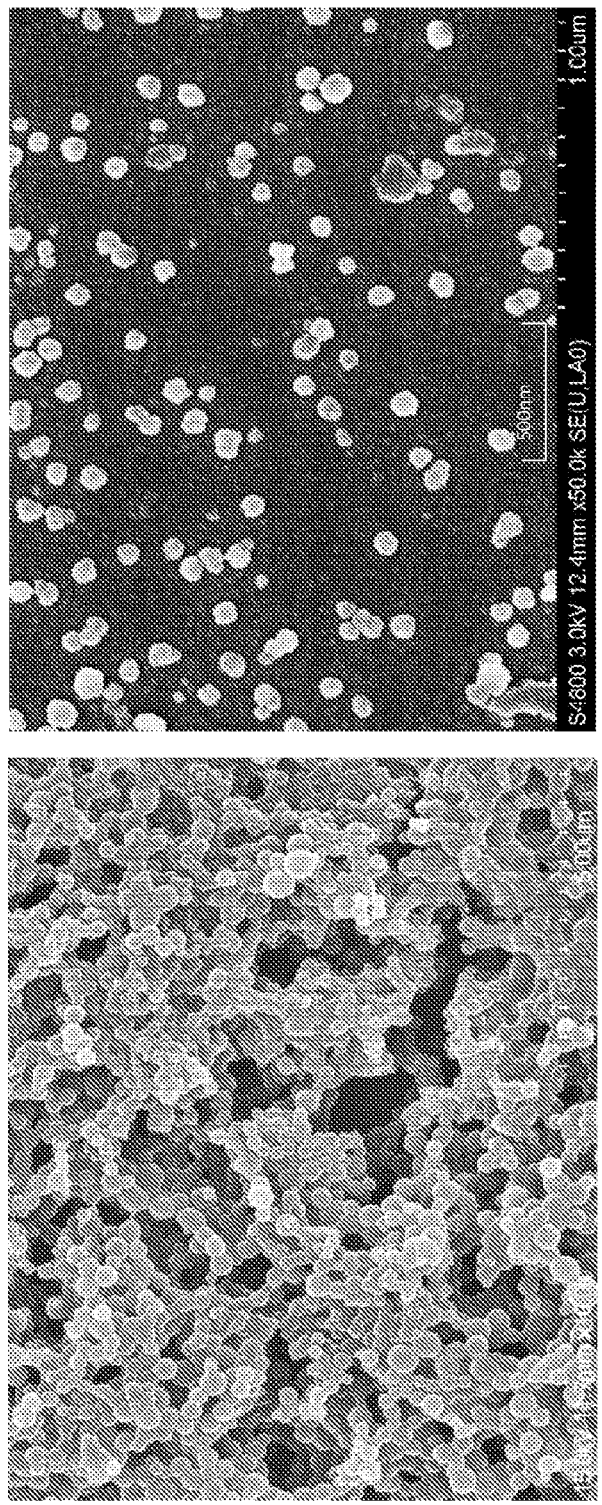
Figure 6. HKP/siRNA formulation: lyophilized nanoparticles (left) and nanoparticles in aqueous solutions (right).

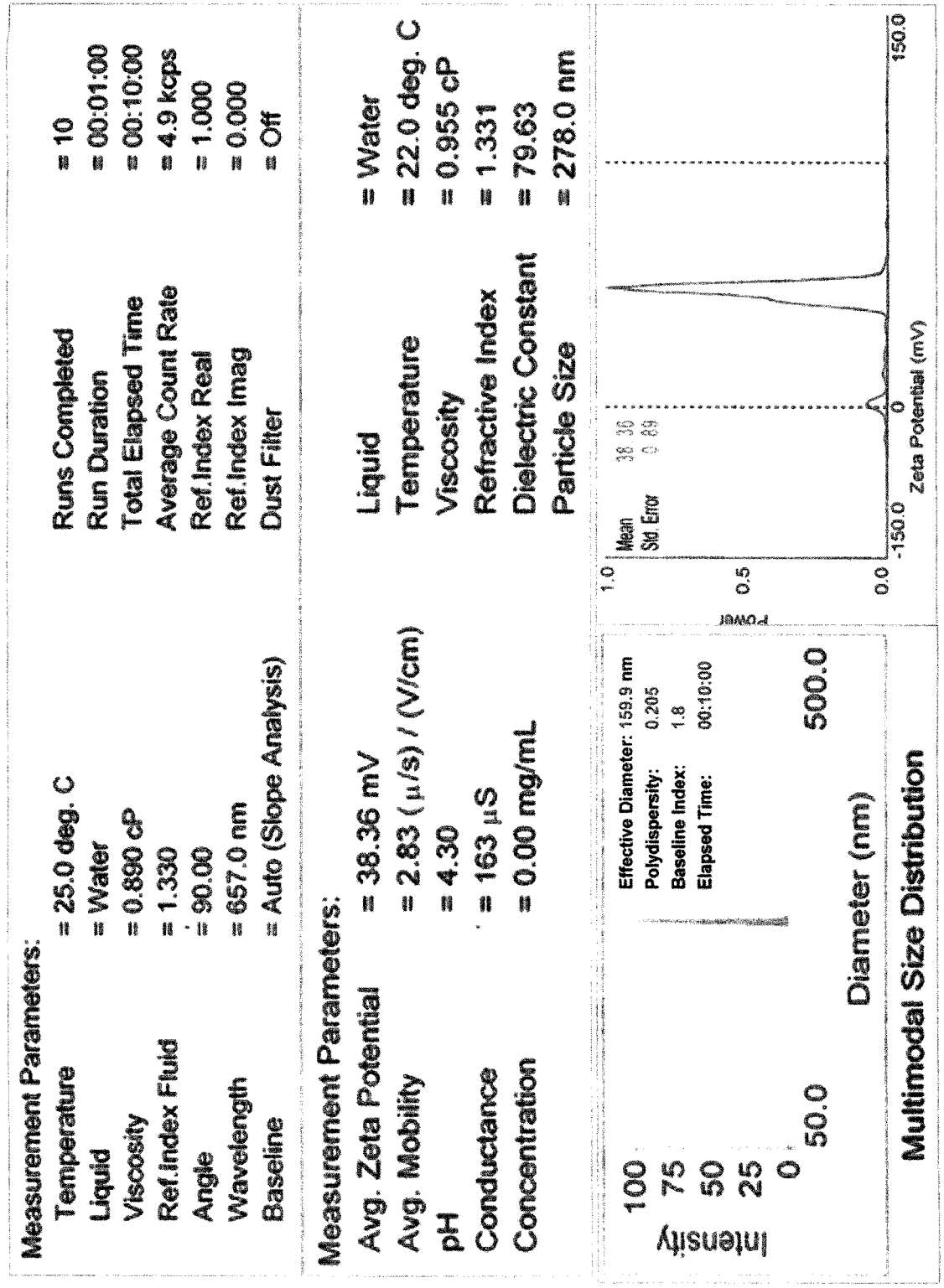
Figure 7. List of physicochemical properties of HKP (siRNA) nanoparticles.

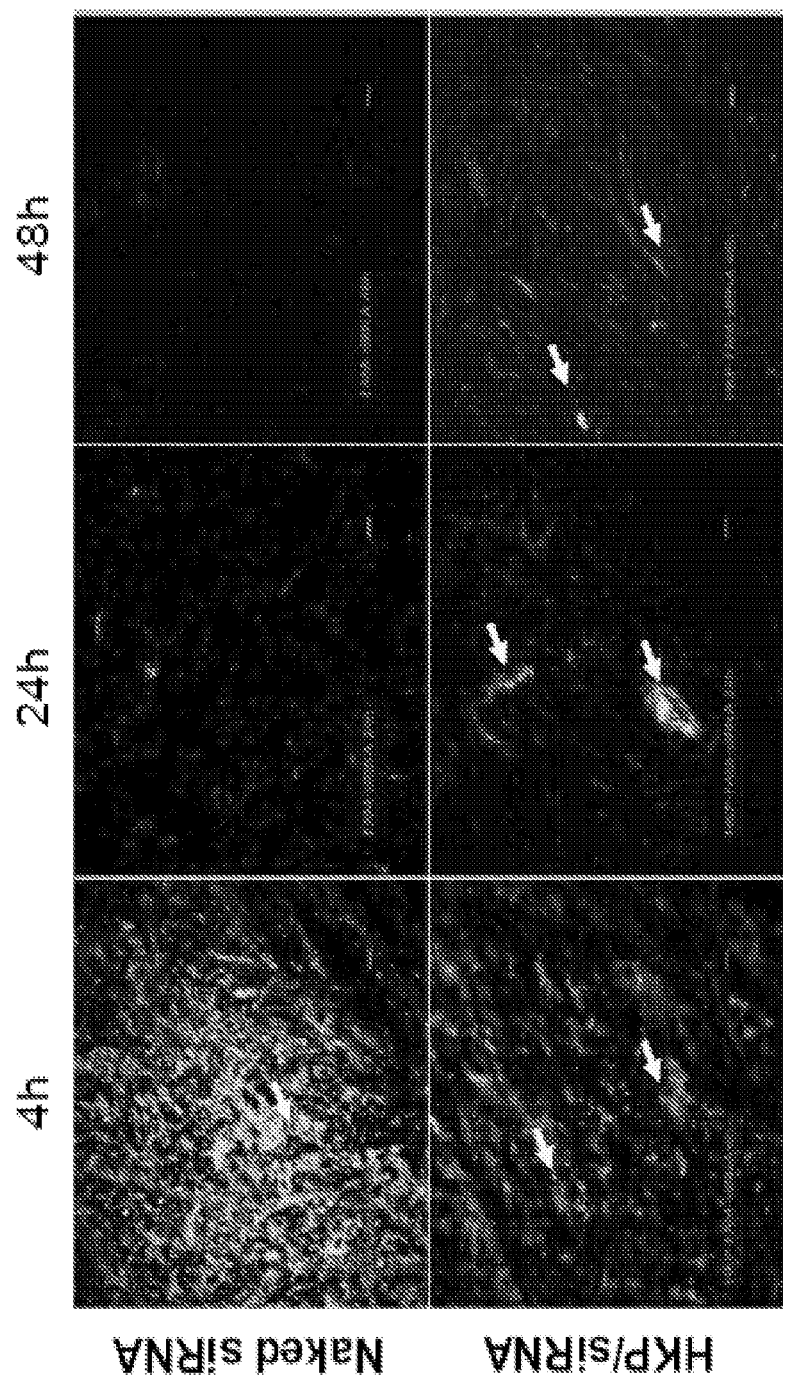
Figure 8. HKP enhanced siRNA delivery in human hypertrophic scar tissue

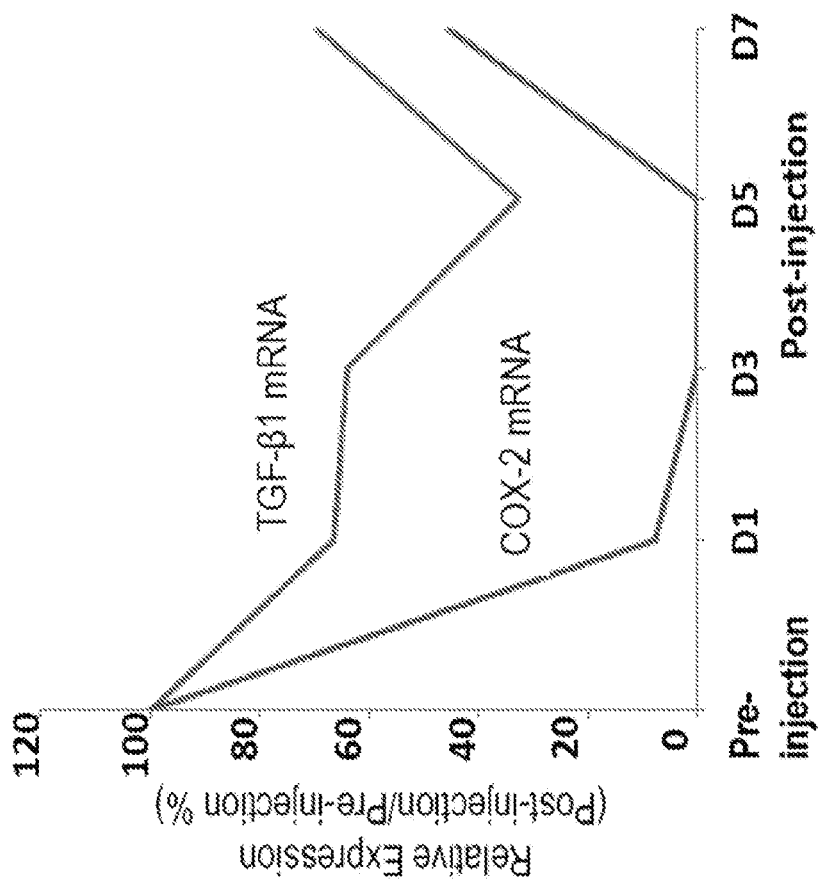
Figure 9. Pharmacokinetics of HKP(TGF-β1/COX-2siRNAs) in human hypertrophic scar tissue

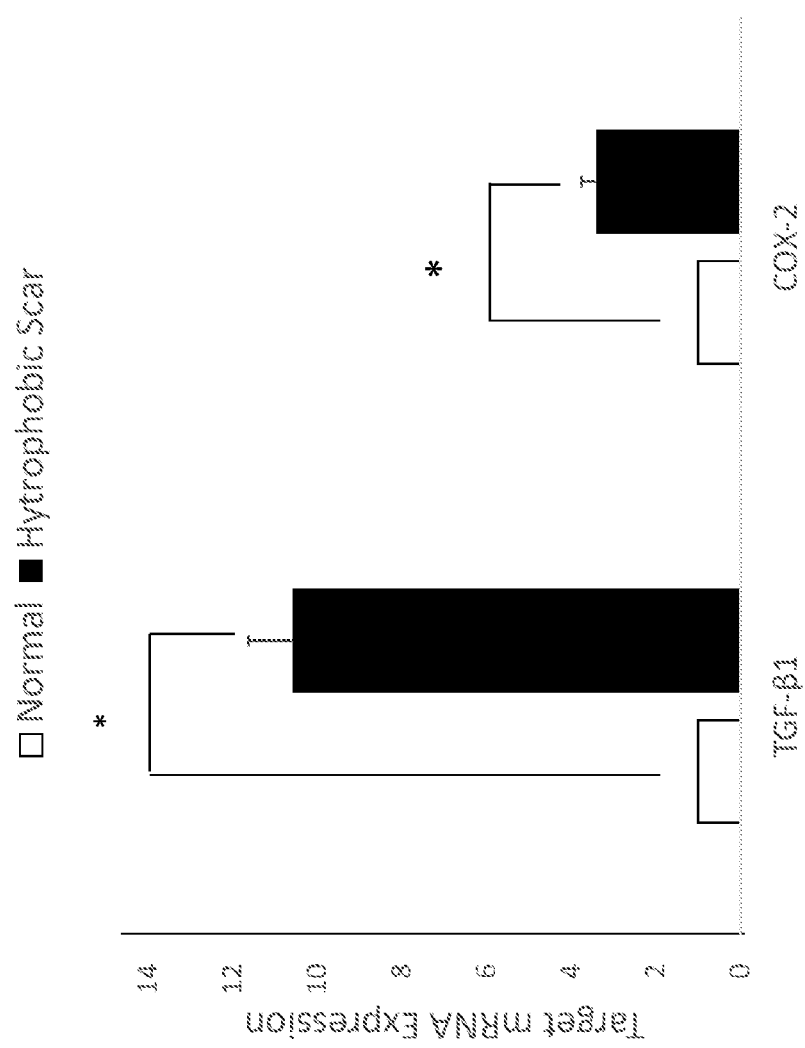
Figure 10. Expressions of TGF-β1 and COX-2 in human hypertrophic scar tissue

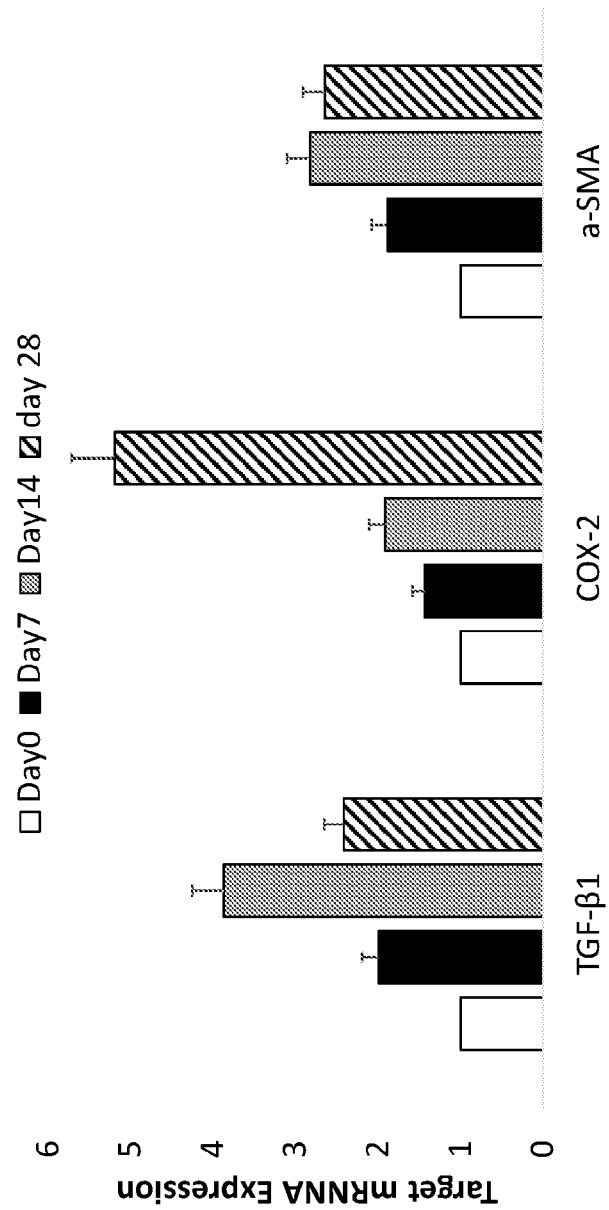
Figure 11. Expressions of TGF-β1 and COX-2 in human hypertrophic scar tissue after implanted onto mouse back.

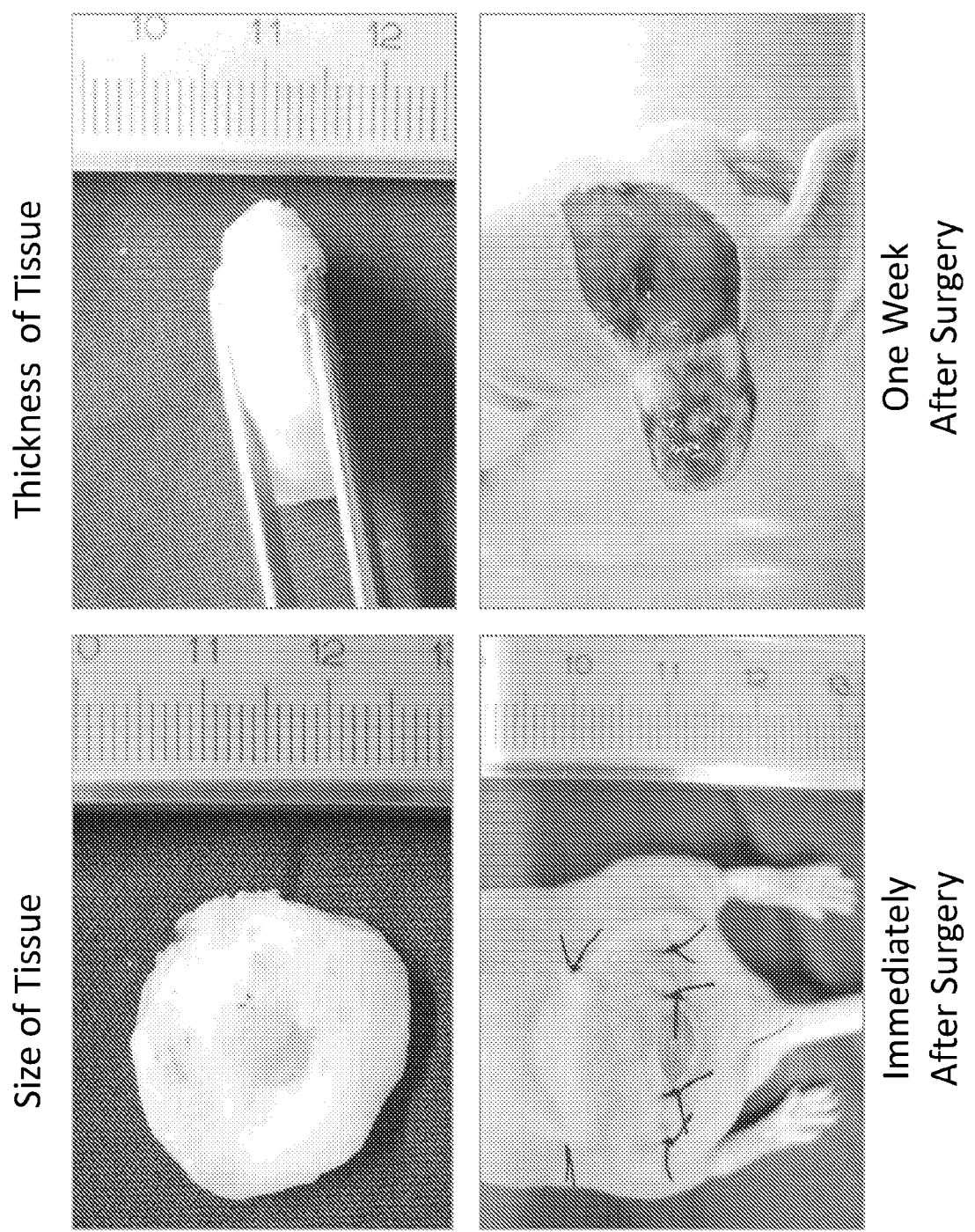
Figure 12 Procedures to establish the hypertrophic scar implant model with mouse

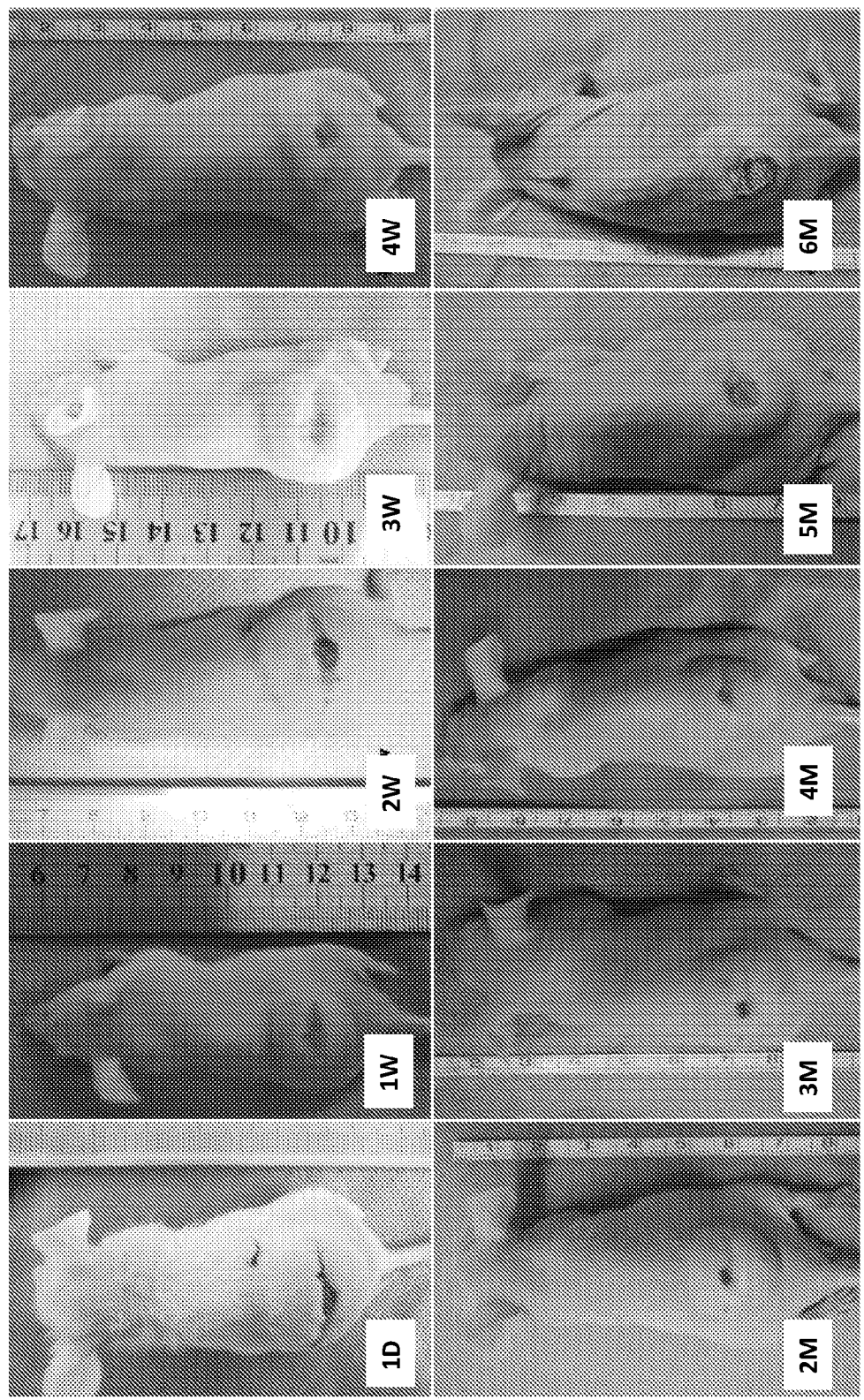
Figure 13 Appearance of implanted hypertrophic scar on the mouse back

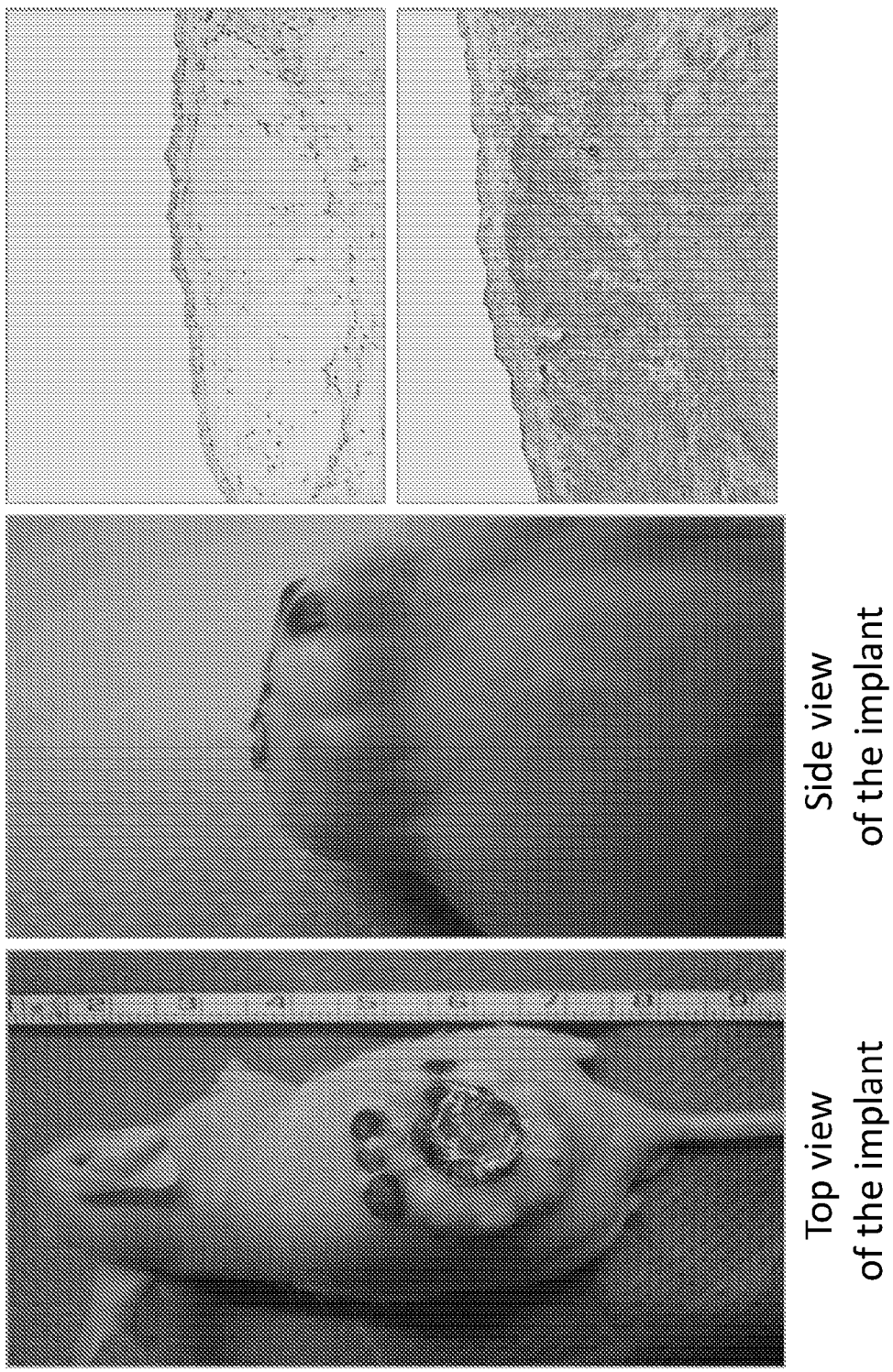
Figure 14 Procedures to establish the hypertrophic scar implant model with mouse

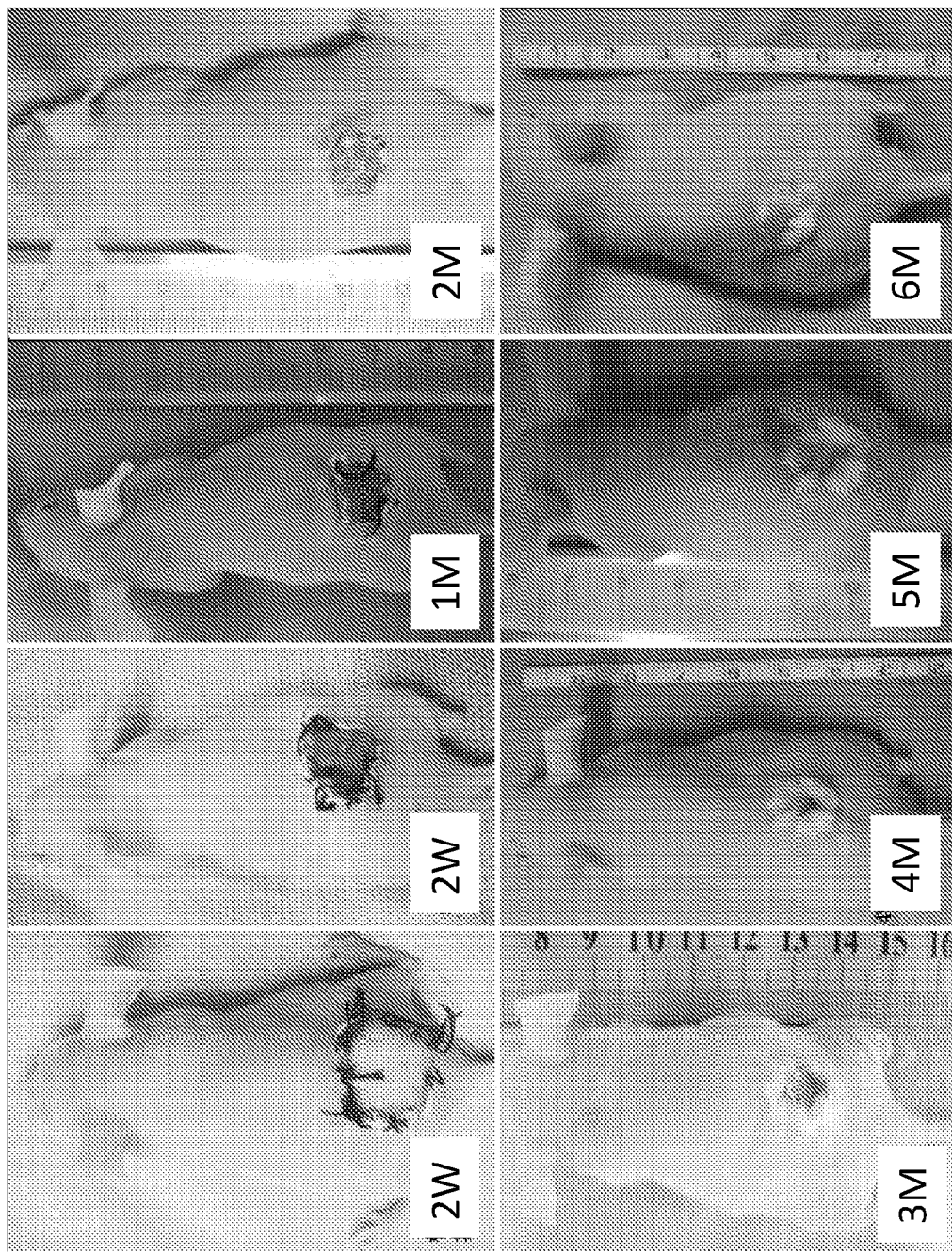
Figure 15 Appearance of implanted skin tissue on the mouse back

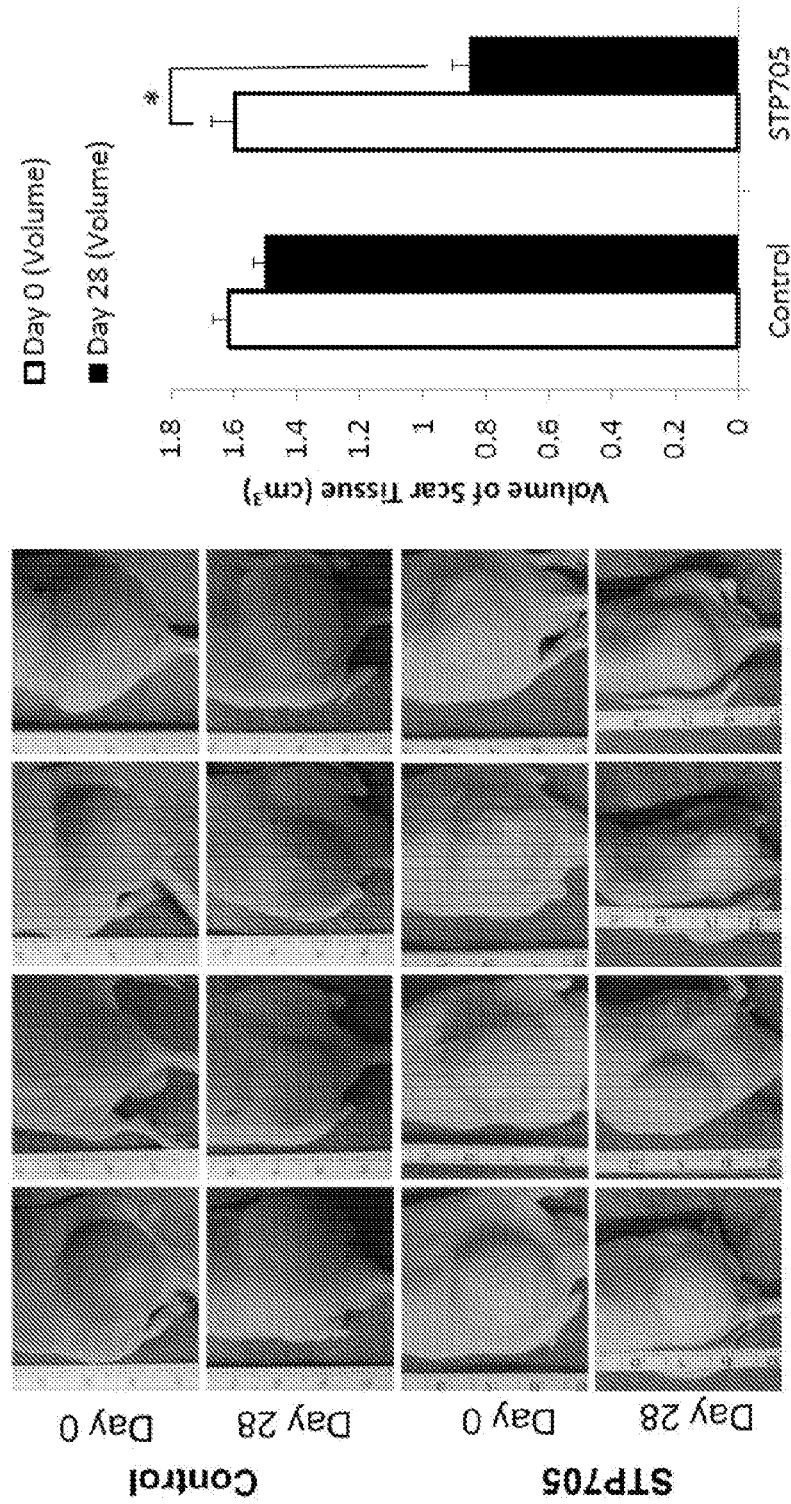
Figure 16. Size reduction of the hypertrophic scar after being treated by HKP/(TGF-β1-COX-2siRNA).

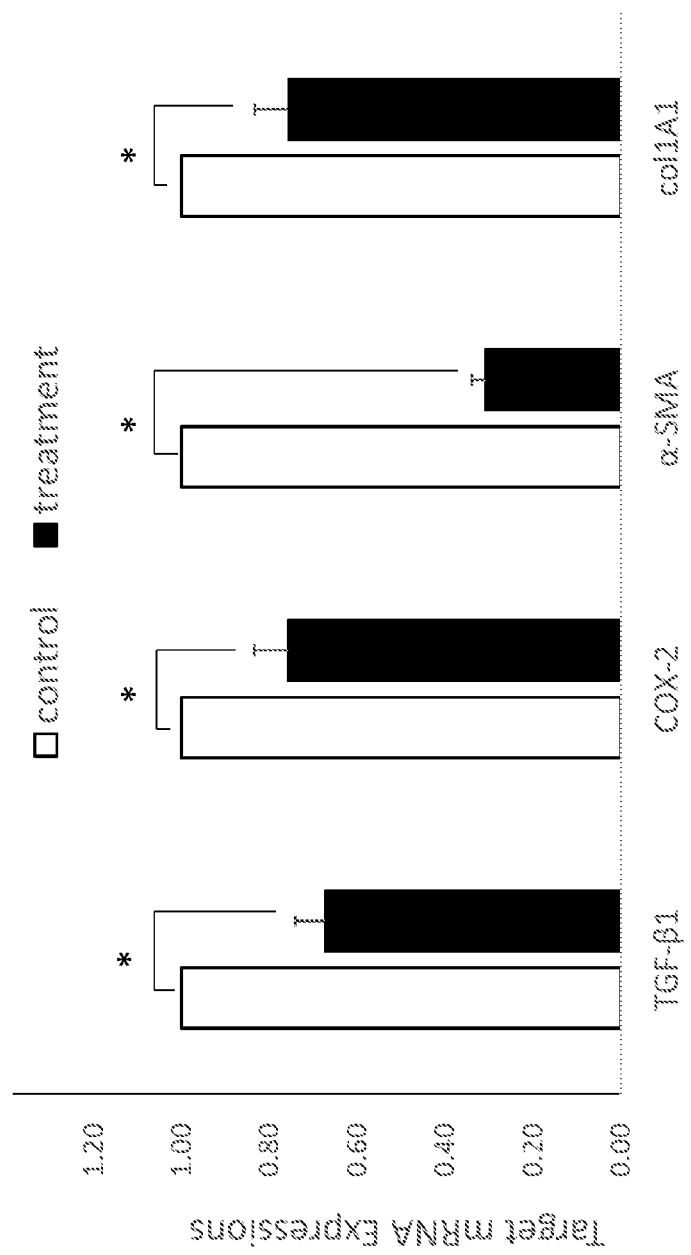
Figure 17. Down Regulation of Target Expression in the hypertrophic scar after being treated by HKP/(TGF-β1-COX-2siRNA).

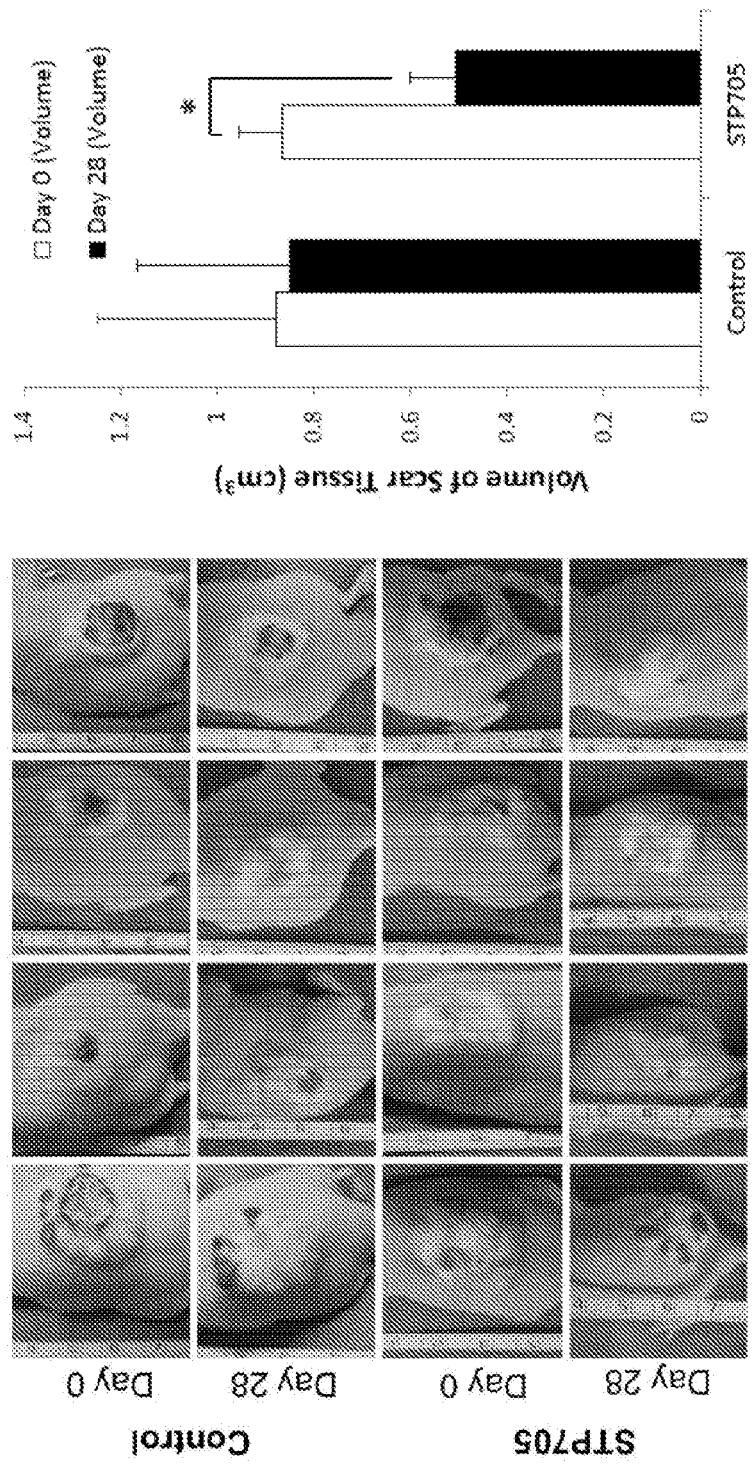
Figure 18. Size reduction of the implanted skin tissue after being treated by HKP/(TGF-β1-COX-2siRNA).

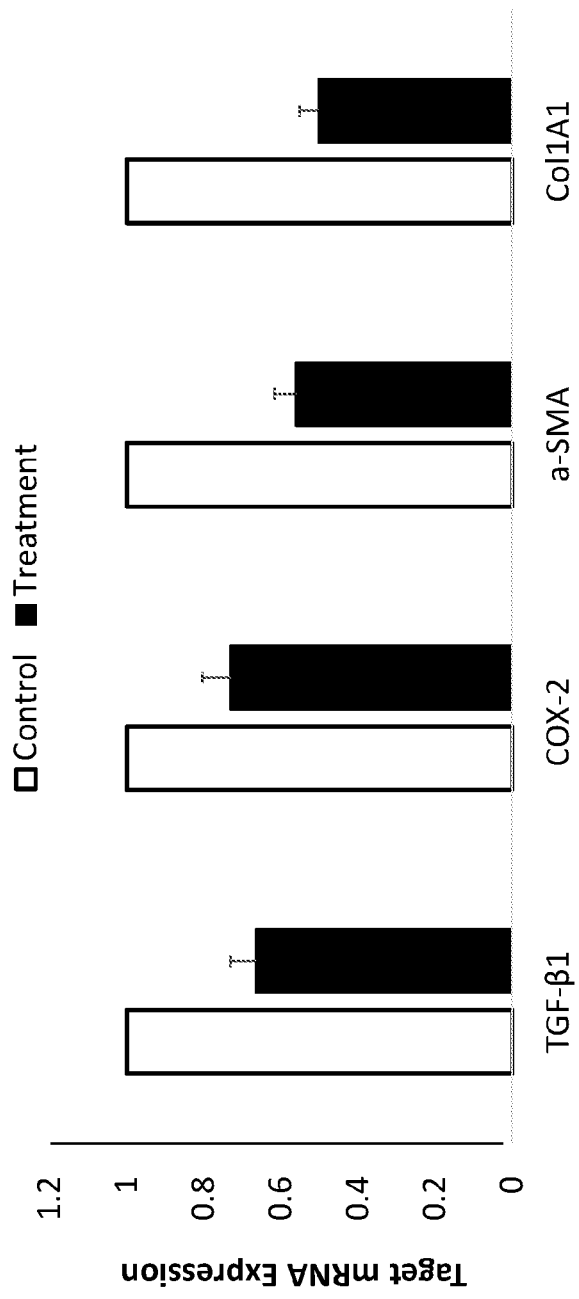
Figure 19. Down Regulation of Target Expression in the implanted skin tissue after being treated by HKP/(TGF-β1-COX-2siRNA).

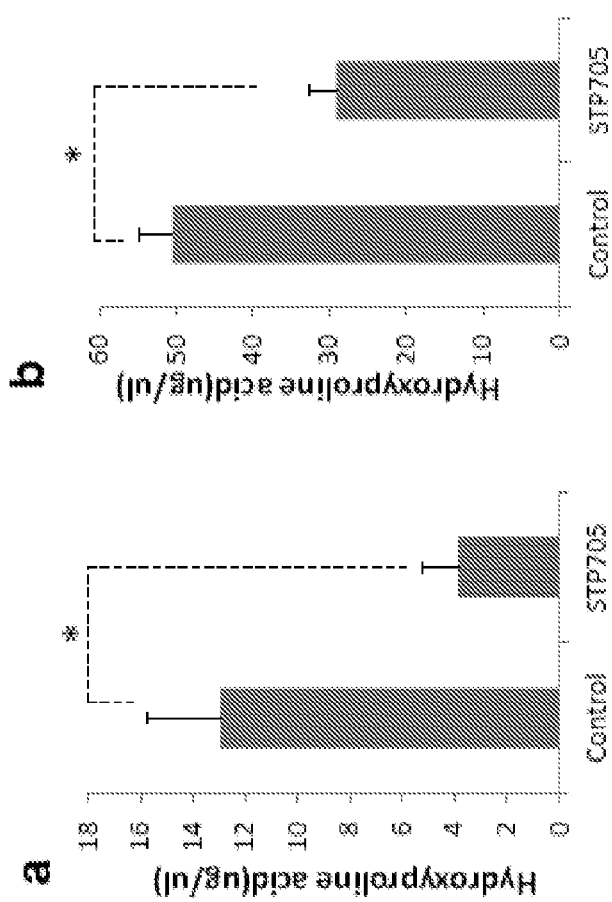
Figure 20. Down Regulation of Hydroxproline acid in the implanted scar tissue (left) and skin tissue (right).

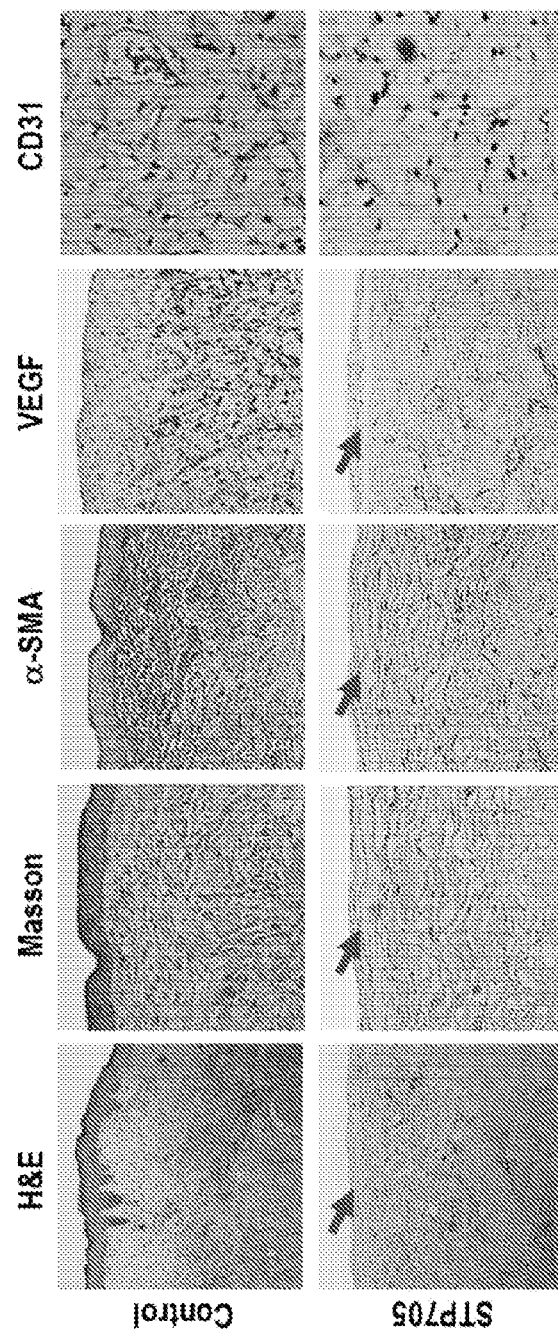
Figure 21. Down Regulation of gene targets in the hypertrophic scar tissues.

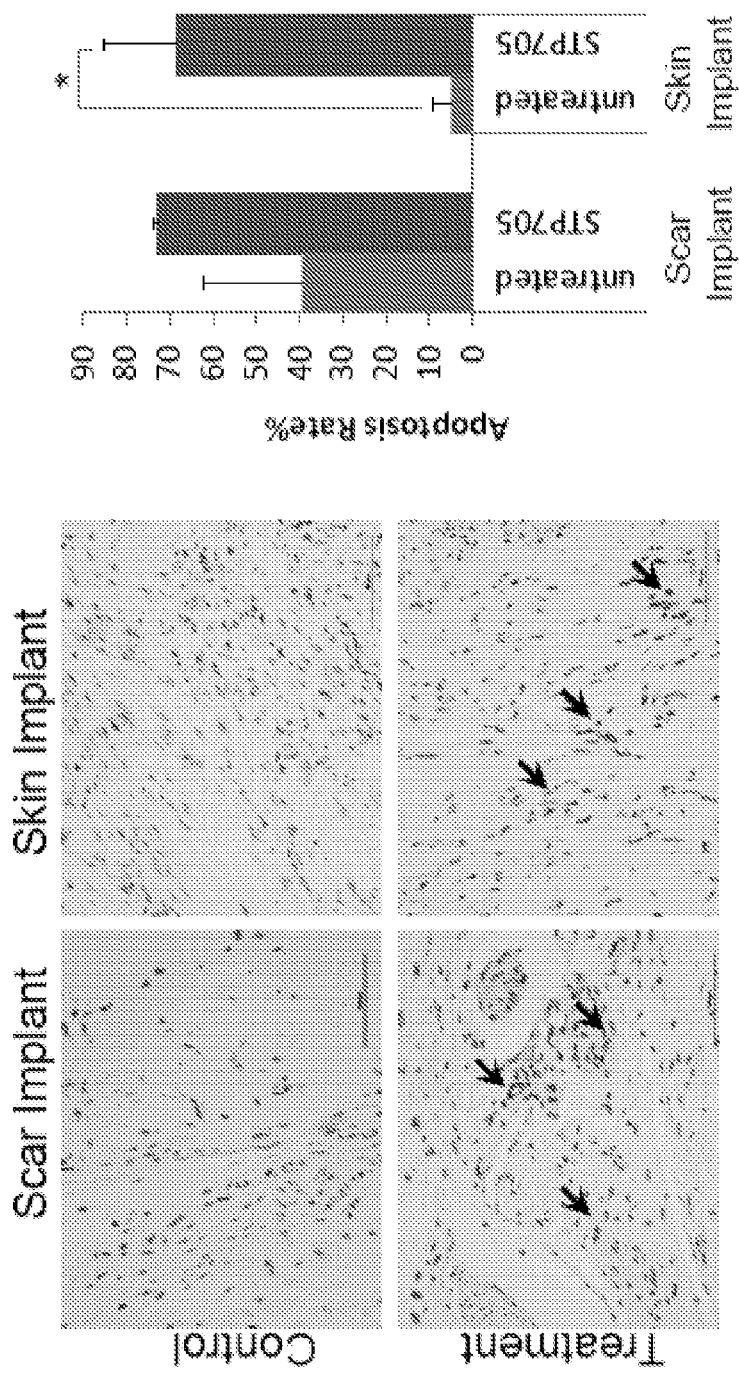
Figure 22. Activation of Apoptosis of fibroblasts/myofibroblasts in the hypertrophic scar and implanted skin tissues. Histology evidence (left) and quantification indexes (right).

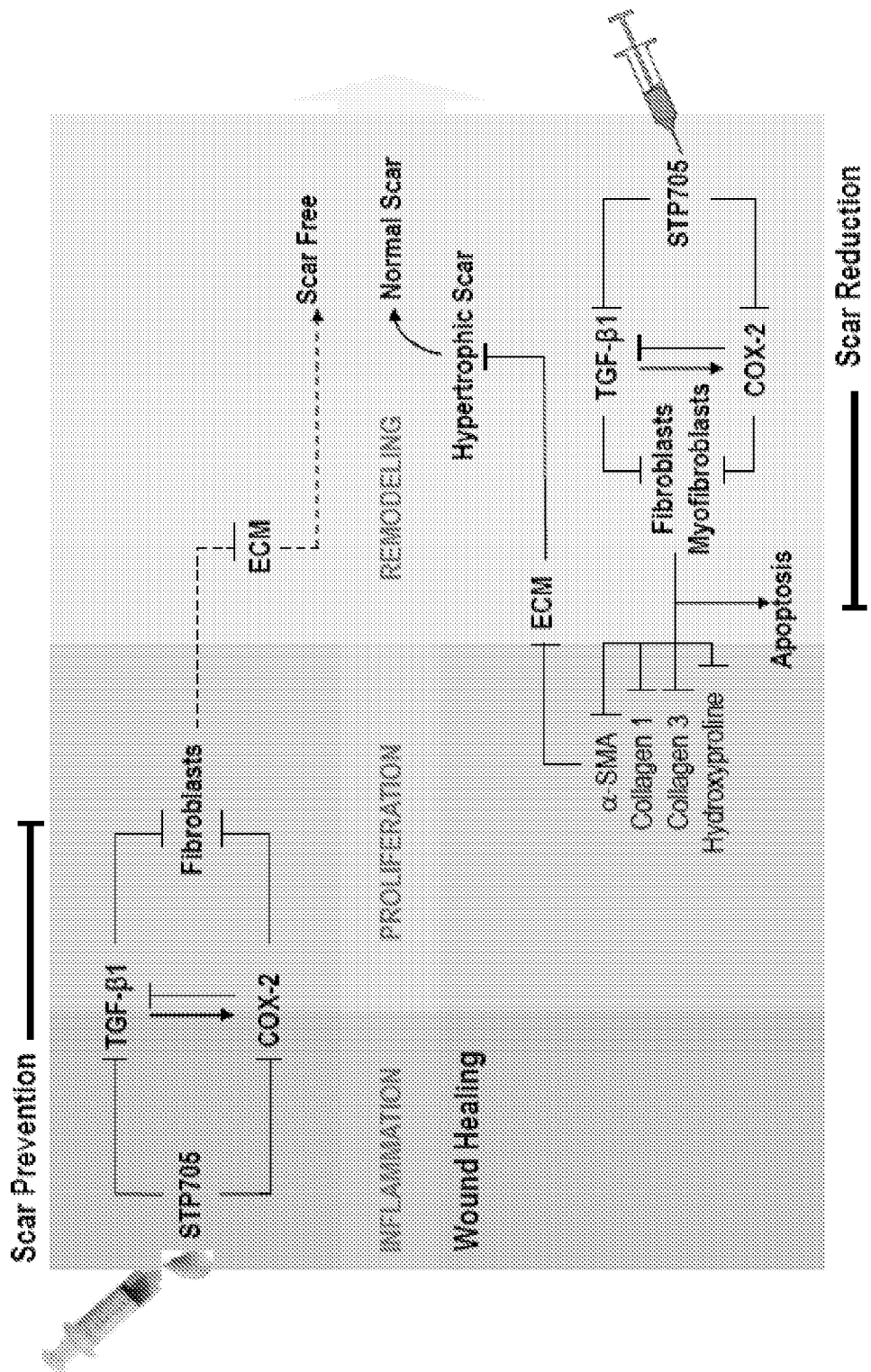
Figure 23. Hypothesis of a schematic mechanism of action for STP705-mediated antifibrotic activity.

SEQUENCE LISTING

```
<160> NUMBER OF SEQ ID NOS: 45

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cccaagggcu accaugccaa cuucu                                              25

<210> SEQ ID NO 2
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
agaaguuggc augguagccc uuggg                                              25

<210> SEQ ID NO 3
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ggucugguGc cuggucugau gaugu                                              25

<210> SEQ ID NO 4
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
acaucaucag accaggcacc agacc                                             25

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys His His His Lys His His His Lys His His His Lys His His His
1               5                   10                  15

Lys

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys His His His Lys His His His Asn His His His Asn His His His
1               5                   10                  15

Asn

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys His His His Lys His His His Lys His His His Lys His His
1               5                   10                  15

His Lys

<210> SEQ ID NO 8
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ggauccacga gcccaagggc uacca                                             25

<210> SEQ ID NO 9
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 9
ccucaauuca gucucucauc ugcaa                                              25

<210> SEQ ID NO 10
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gauccacgag cccaagggcu accau                                              25

<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
cacgagccca agggcuacca ugcca                                              25

<210> SEQ ID NO 12
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gaggucaccc gcgugcuaau ggugg                                              25

<210> SEQ ID NO 13
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
guacaacagc acccgcgacc gggug                                              25

<210> SEQ ID NO 14
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
guggauccac gagcccaagg gcuac                                              25

<210> SEQ ID NO 15
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 15
gagcaccauu cuccuugaaa ggacu                                            25

<210> SEQ ID NO 16
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ccucaauuca gucucucauc ugcaa                                            25

<210> SEQ ID NO 17
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gauguuugca uucuuugccc agcac                                            25

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gucuuugguc uggugccugg ucuga                                            25

<210> SEQ ID NO 19
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gugccugguc ugaugaugua ugcca                                            25

<210> SEQ ID NO 20
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
caccauucuc cuugaaagga cuuau                                            25

<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
caauucaguc ucucaucugc aauaa                                              25

<210> SEQ ID NO 22
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ugguagcccu ugggcucgug gaucc                                              25

<210> SEQ ID NO 23
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
uugcagauga gagacugaau ugagg                                              25

<210> SEQ ID NO 24
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
augguagccc uugggcucgu ggauc                                              25

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uggcauggua gcccuugggc ucgug                                              25

<210> SEQ ID NO 26
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
agaaguuggc augguagccc uuggg                                              25

<210> SEQ ID NO 27
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27

```
cacccggucg cgggugcugu uguac                                         25
```

<210> SEQ ID NO 28
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28

```
guagcccuug ggcucgugga uccac                                         25
```

<210> SEQ ID NO 29
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29

```
aguccuuuca aggagaaugg ugcuc                                         25
```

<210> SEQ ID NO 30
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30

```
uugcagauga gagacugaau ugagg                                         25
```

<210> SEQ ID NO 31
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31

```
gugcugggca aagaaugcaa acauc                                         25
```

<210> SEQ ID NO 32
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32

```
ucagaccagg caccagacca aagac                                         25
```

<210> SEQ ID NO 33
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uggcauacau caucagacca ggcac                                              25

<210> SEQ ID NO 34
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
auaaguccuu ucaaggagaa uggug                                              25

<210> SEQ ID NO 35
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uuauugcaga ugagagacug aauug                                              25

<210> SEQ ID NO 36
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
cccaagggcu accaugccaa cuucu                                              25

<210> SEQ ID NO 37
<211> LENGTH: 25
<212> TYPE: RNA
<213> ORGANISM: Homo sapiens

<400> SEQUENCE: 37
cccaagggcu accaugccaa cuucu                                              25

<210> SEQ ID NO 38
<211> LENGTH: 25
<212> TYPE: RNA
<213> ORGANISM: Mus sp.

<400> SEQUENCE: 38
cccaagggcu accaugccaa cuucu                                              25

<210> SEQ ID NO 39
<211> LENGTH: 25
<212> TYPE: RNA
<213> ORGANISM: Macaca sp.

<400> SEQUENCE: 39
cccaagggcu accaugccaa cuucu                                              25

<210> SEQ ID NO 40
<211> LENGTH: 25
<212> TYPE: RNA
<213> ORGANISM: Sus scrofa

<400> SEQUENCE: 40

```
cccaagggcu accaugccaa uuucu                                              25

<210> SEQ ID NO 41
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41 ggucggugc cuggucugau gaugu                                               25

<210> SEQ ID NO 42
<211> LENGTH: 25
<212> TYPE: RNA
<213> ORGANISM: Homo sapiens

<400> SEQUENCE: 42 ggucggugc cuggucugau gaugu                                               25

<210> SEQ ID NO 43
<211> LENGTH: 25
<212> TYPE: RNA
<213> ORGANISM: Mus sp.

<400> SEQUENCE: 43 ggucggugc cuggucugau gaugu                                               25

<210> SEQ ID NO 44
<211> LENGTH: 25
<212> TYPE: RNA
<213> ORGANISM: Macaca sp.

<400> SEQUENCE: 44 ggucggugc cuggucugau gaugu                                               25

<210> SEQ ID NO 45
<211> LENGTH: 25
<212> TYPE: RNA
<213> ORGANISM: Sus scrofa

<400> SEQUENCE: 45 ggucggugc cuggucugau gaugu                                               25
```

PHARMACEUTICAL COMPOSITIONS AND METHODS OF USE FOR ACTIVATION OF HUMAN FIBROBLAST AND MYOFIBROBLAST APOPTOSIS

CROSS-REFERENCE TO RELATED PATENT APPLICATION

This application claims the benefit of and priority to U.S. Provisional Patent Application No. 62/414,780, filed Oct. 30, 2016, which is incorporated herein by reference in its entirety.

SEQUENCE LISTING

The instant application contains a Sequence Listing which has been filed electronically in ASCII format and is hereby incorporated by reference in its entirety. Said ASCII copy, created on May 6, 2019, is named SIR-017_P001-US_SL.txt and is 10,400 bytes in size.

FIELD OF THE INVENTION

The current invention relates to pharmaceutical compositions and methods for the activation of human fibroblast and myofibroblast apoptosis.

BACKGROUND

Human hypertrophic scar reduction and management are among the major therapeutic challenges due to lack of in-depth understanding of the underlying mechanism and the few validated treatment strategies available (Mustoe et al, 2002). Understanding the pathophysiology of fibrosis may lead to a novel therapeutic with improved clinical benefit (Wynn et al, 2012). Fibrosis is defined by excessive accumulation of extracellular matrix (ECM) in and around the damaged tissue, which can lead to permanent scarring (Miller et al, 2005). Hypertrophic scar (HTS) is the result of a disrupted balance between ECM protein deposition and degradation during the dermal wound healing process (Zhu et al, 2013). It is characterized by the prolonged inflammatory response to injury resulting in an increased vascularization, hypercellularity and excessive collagen deposition from local fibroblasts (Tredget et al, 1997). Fibroblasts are the most common cells in connective tissue, playing a key role in the wound healing process and can differentiate into myofibroblasts that results in increased ECM synthesis and tissue contraction (McDougall et al, 2006 and Nedelec et al, 2001).

Many treatment modalities for excessive scarring have not achieved satisfying remission. Those treatments included surgical excision, radiation, corticosteroid injections, cryotherapy, laser vaporization, topical 5-fluorouracil, bleomycin injection, paper tape to eliminate scar tension, pressure garment therapy, silicone gel sheeting, and short term use of ozonated oil. Thus, there is a need for a new treatment to reduce hypertrophic scars in humans.

We have developed a process to formulate Histidine-Lysine co-Polymer (HKP) with selected siRNA duplexes targeting both TGF-β1 and COX-2 into an aqueous nanoparticle formulation. Delivery of this HKP/siRNA nanoparticle formulation through intra-dermal injection, revealed a synergistic effect of size reduction of excessive scars. This dual-targeted siRNA therapeutic approach exhibits potent anti-fibrotic activity through a newly discovered mechanism of action.

BRIEF DESCRIPTION OF THE FIGURES

FIG. 1: Two potent siRNA duplexes targeting TGF-β1 and COX-2 respectively were selected using qRT-PCR analyses following cell transfections with corresponding siRNA dupelxes and total RNA solation. The selected siRNA duplexes targeting TGF-β1 and COX-2 exhibited high homology to their corresponding gene sequences of human, mouse, monkey and pig. FIG. 1 discloses the TGF-β1 sequences as SEQ ID NOS 36-40 and the COX-2 sequences as SEQ ID NOS 41-45, all respectively, in order of appearance.

FIG. 2: Comparisons of target gene (TGF-β1, COX-2, α-SMA, Col1A1 and Col3A1) mRNA expressions in human fibroblast cells after transfections with the TGF-β1$_{siRNA}$, or COX-2$_{siRNA}$, or TGF-β1/COX-2$_{siRNAs}$ at 5 μg/ml (*P<0.05, **p<0.01). The total RNA samples were collected for each treated cell culture plate followed with qRT-PCR analysis. The results were demonstrated in the figure with error bars and statistic significant indicators. Where NS represents non-specific siRNA treatment control.

FIG. 3. Electron microscope images (SEM) of the fibroblast cells transfected with the TGF-β1/COX-2$_{siRNAs}$ illustrates an strong apoptotic activity, where N indicates nucleus, black arrows indicate Lipid-siRNA particles and red arrows indicate apoptosis bodies.

FIG. 4. (Left) FACS analysis indicates significant increase of apoptotic cell population of human myofibroblasts when TGF-β1/COX-2$_{siRNAs}$ was transfected simultaneously, as seen in the right lower panel, in comparison with the untreated and treated with the individual siRNA. (Right) Four different stages of treated fibroblasts: dying cells, apoptotic cells, viable cells and viable apoptotic cells. The cells treated with TGF-β1/COX-2 siRNA in combination resulted in significant up regulation of apoptosis. Primary fibroblasts were treated with reagents as previously described (5 μg/ml each). Annexin V/PI assay for apoptosis was conducted according to manufacturer's instruction (Invitrogen, CA). FACS data were presented here as means.

FIG. 5. (Left) Antibody staining specifically against α-SMA protein demonstrated a remarkable decrease of the protein expression with a TGF-β1/COX-2$_{siRNAs}$ treatment, in comparison with groups treated with either TGF-β1$_{siRNA}$ or COX-2$_{siRNA}$ alone. (Right) Hydroxyproline acid activity were significantly down regulated (*P<0.05) with treatments of TGF-β1$_{siRNA}$, or COX-2$_{siRNA}$, or TGF-β1/COX-2$_{siRNAs}$. Among them TGF-β1/COX-2$_{siRNAs}$ demonstrated a more potent inhibitory activity.

FIG. 6. (Left) SEM image of HKP (siRNA) nanoparticles were in a lyophilized form for long time storage and easy transportation. The nanoparticles were analyzed with a particle sizer (Brookhaven 190, N.Y., USA) and resulted in an average size of 150 nm±30 in diameter. (Right) SEM image of HKP (TGF-β1/COX-2$_{siRNAs}$) nanoparticles in aqueous solution exhibited an average size of 150 nm in diameter for injectable administration.

FIG. 7. List of physicochemical properties of HKP (siRNA) nanoparticles have indicated that the particle sizes (upper panel and lower left) and zeta-potentials of HKP (siRNA) nanoparticles (middle panel and lower right) were measured, resulted in an average particles size about 150 nm in diameter, with Zeta-potentials of 38 vM.

FIG. 8. Comparison between Alexa Fluor labeled siRNA and HKP-packaged the same siRNA in vivo for their duration and dispersion after intra-scar injection. Samples collected from a human hypertrophic scar tissue implant model of mice, at 0, 24 and 48 hour time points post administrations.

FIG. 9. The qRT-PCR results reveal significant upregulated expressions of TGF-β1 and COX-2 in human HTS tissue, comparing to those in normal human skin tissue. *P<0.05 (N=4).

FIG. 10. Injections of HKP (TGF-β1/COX-2$_{siRNAs}$) nanoparticle solution into the human hypertrophic scar resulted in down regulations of TGF-β1 and COX-2 expressions in the tissue. This target gene silencing activity lasts up to 5 days, based on the qRT-PCR analyses following the one-shot administration.

FIG. 11. Expression dynamics of TGF-β1, COX-2 and α-SMA in human HTS tissue after being implanted, at day 0, 7, 14 and 28 (N=3), have been evaluated. Interestingly, the peak level of TGF-β1 expression was on day 14. The COX-2 expression kept continuing increase until day 28. Meanwhile, the α-SMA expression pattern was similar as the TGF-β1 expression.

FIG. 12. The process for establishing a human hypertrophic scar implant mouse model. The size and thickness of the human hypertrophic scar tissue used for nude mouse implantation. The appearance after the scar tissue implanted and the wound site closed. Key improvement to the original procedures for establishing such a model was that several stitches were performed to fix transplant to the skin pocket. The human HTS transplant became very much viable when dissected one week later as seen with enrich blood vessel network.

FIG. 13. Appearance images after the human hypertrophic scar implanted provided an overview of appearances after the implanted tissue from day 1, one-week, two-week, three-week, four-week, one-month and all the way to six-month.

FIG. 14. A close view of human skin implant on nude mouse shows both top and side views of a human skin sample implanted onto the nude mouse back. The tissue samples were collected and stained with H&E showing the implanted tissue has grown into the surrounding tissues.

FIG. 15. The overview of the appearances of human skin tissue implanted onto nude mouse back, from two weeks to six months after the implantation. The observations was started from 2 weeks to 1 month, 2 month, 3 month, and all the way to 6 month.

FIG. 16. Images of human HTS implants, either treated with HKP (TGF-β1/COX-2$_{siRNAs}$) or control solution, at day 0 and 28 post treatments. (d) The reduction of the scar tissue sizes about 45% for HKP (TGF-β1/COX-2$_{siRNAs}$) treated group (N=4), *P<0.05. (e) Expressions of TGF-β1, COX-2, α-SMA and Col1A1 mRNAs in the HKP (TGF-β1/COX-2$_{siRNAs}$) treated scar implants, N=3, *P<0.05.

FIG. 17. The reduction of the scar tissue sizes about 45% for HKP (TGF-β1/COX-2$_{siRNAs}$) treated group (N=4), *P<0.05. (e) Expressions of TGF-β1, COX-2, α-SMA and Col1A1mRNAs in the HKP (TGF-β1/COX-2$_{siRNAs}$) treated scar implants, N=3, *P<0.05.

FIG. 18. (Left) Images of human skin implants, either treated with HKP (TGF-β1/COX-2$_{siRNAs}$) or control aqueous solution, at day 0 and day 28$^{th}$ post treatments. (Right) Quantitative illustration of the size changes of the human skin implants. The reduction of the skin tissue sizes reaches up to 38% for HKP (TGF-β1/COX-2$_{siRNAs}$) treated group (N=4), *P<0.05.

FIG. 19. Expressions of TGF-β1, COX-2, α-SMA and Col1A1 mRNAs in the HKP (TGF-β1/COX-2$_{siRNAs}$) treated skin implants, were significantly down regulated (n=3). *P<0.05.

FIG. 20. After HKP (TGF-β1/COX-2$_{siRNAs}$) treatment, we observed 70% down regulations of hydroxyproline acid in human scar tissue implants (a) and 40% in human skin tissue implants (b), N=3, *P<0.05.

FIG. 21. Tissue samples with H&E and Masson's trichrome staining, and IHC staining with antibodies against human VEGF, CD31 and α-SMA proteins, revealed down regulations of the angiogenesis, micro blood vessel marker and fibrogenesis after repeated treatments with HKP (TGF-β1/COX-2$_{siRNAs}$). Red arrows indicate epidermis layer of the skin.

FIG. 22. HKP (TGF-β1/COX-2$_{siRNAs}$) treatment induces activations of fibroblast and myofibroblast apoptosis (black arrows) in those implanted HTS tissues and skin tissues, as showed in the images on the left and quantitative measurements on the right.

FIG. 23. Schematic demonstration of a novel mechanism for prevention and reduction of skin fibrotic scarring. A normal skin wound healing process includes three phases: inflammation, proliferation and remodeling. Scar Prevention: STP705 treatment results in down regulation of TGF-β1 and COX-2 expressions and a fine-tuned fibroblast proliferation, which maintains a balance between deposition and degradation of ECM and promotes a scar-free wound healing. Scar Reduction: An optimal dosing of STP705 is expected to down regulate TGF-β1 and COX-2 expressions in the scar tissue, resulting in apoptosis activation of fibroblasts/myofibroblasts within the scar tissue. The therapeutic effect of STP705 is to reverse fibrotic scarring and reduce hypertrophic scar.

DESCRIPTION OF THE INVENTION

The current invention provides a composition comprising an siRNA molecule that binds to an mRNA that codes for TGFβ1 protein in a mammalian cell, an siRNA molecule that binds to an mRNA that codes for COX-2 protein in a mammalian cell, and a pharmaceutically acceptable carrier comprising a pharmaceutically acceptable histidine-lysine co-polymer. The current invention also provides methods of using the composition. In one embodiment, it provides a method of down-regulating pro-fibrotic factors and fibrotic pathways in the cells of a tissue of a mammal, comprising administering to the tissue a therapeutically effective amount of the composition. In another embodiment, it provides a method of activating fibroblast and myofibroblast apoptosis in a tissue of a mammal, comprising administering to the tissue a therapeutically effective amount of the composition. In still another embodiment, it provides a method of reducing the size of a hypertrophic scar in the tissue of a mammal, comprising administering to the scar a therapeutically effective amount of the composition. In still another embodiment, the invention provides a method of reducing fibrosis in the tissue of a mammal, comprising administering to the tissue a therapeutically effective amount of the composition.

The siRNA molecules can produce additive or synergistic effects in the cells, depending on the compositions and structures of the particular molecules. In a preferred embodiment, they produce a synergistic effect.

As used herein, an "siRNA molecule" is a duplex oligonucleotide, that is a short, double-stranded polynucleotide, that interferes with the expression of a gene in a cell that produces RNA, after the molecule is introduced into the cell.

For example, it targets and binds to a complementary nucleotide sequence in a single stranded (ss) target RNA molecule, such as an mRNA or a micro RNA (miRNA). The target RNA is then degraded by the cell. Such molecules are constructed by techniques known to those skilled in the art. Such techniques are described in U.S. Pat. Nos. 5,898,031, 6,107,094, 6,506,559, 7,056,704 and in European Pat. Nos. 1214945 and 1230375, which are incorporated herein by reference in their entireties. By convention in the field, when an siRNA molecule is identified by a particular nucleotide sequence, the sequence refers to the sense strand of the duplex molecule.

The siRNA molecule can be made of naturally occurring ribonucleotides, i.e., those found in living cells, or one or more of its nucleotides can be chemically modified by techniques known in the art. In addition to being modified at the level of one or more of its individual nucleotides, the backbone of the oligonucleotide can be modified. Additional modifications include the use of small molecules (e.g. sugar molecules), amino acid molecules, peptides, cholesterol, and other large molecules for conjugation onto the siRNA molecule.

In one embodiment, the molecule is an oligonucleotide with a length of about 19 to about 35 base pairs. In one aspect of this embodiment, the molecule is an oligonucleotide with a length of about 19 to about 27 base pairs. In another aspect, the molecule is an oligonucleotide with a length of about 21 to about 25 base pairs. In all of these aspects, the molecule may have blunt ends at both ends, or sticky ends at both ends, or a blunt end at one end and a sticky end at the other.

In the composition of the invention, the relative amounts of the two different molecules and the copolymer can vary. In one embodiment, the ratio of the two different siRNA molecules is about 1:1 by mass. In another embodiment, the ratio of these molecules to the copolymer is about 1:4, 1:4.5, or 1:5 by mass. Preferably, the ratio of the two different siRNA molecules is about 1:1 by mass and the ratio of these molecules to the copolymer is about 1:4, 1:4.5, or 1:5 by mass. With these ratios, the composition forms nanoparticles with an average size of about 150 nm in diameter.

In one embodiment, the siRNA molecules are selected from the ones identified in Table 1. An example is the pair designated hmTF-25-2 and hmCX-25-1 in the table, which has the following sequences:

```
hmTF-25-2:
                                           (SEQ ID NO: 1)
sense, 5'-r(CCCAAGGGCUACCAUGCCAACUUCU)-3', (SEQ ID NO: 2)
antisense, 5'-r(AGAAGUUGGCAUGGUAGCCCUUGGG)-3', and
hmCX-25-1:
                                           (SEQ ID NO: 3)
sense, 5'-r(GGUCUGGUGCCUGGUCUGAUGAUGU)-3', (SEQ ID NO: 4)
antisense, 5'-r(ACAUCAUCAGACCAGGCACCAGACC)-3'.
```

The invention includes a method for identifying the desired siRNA molecules comprising the steps of: (a) creating a collection of siRNA molecules designed to target a complementary nucleotide sequence in the target mRNA molecules, wherein the targeting strands of the siRNA molecules comprise various sequences of nucleotides; (b) selecting the siRNA molecules that show the highest desired effect against the target mRNA molecules in vitro; (c) evaluating the selected siRNA molecules in an animal wound model; and (d) selecting the siRNA molecules that show the greatest efficacy in the model for their silencing activity and therapeutic effect.

Importantly, it is presently not possible to predict with high degree of confidence which of many possible candidate siRNA sequences potentially targeting an mRNA sequence of a disease gene will, in fact, exhibit effective RNAi activity. Instead, individually specific candidate siRNA polynucleotide or oligonucleotide sequences must be generated and tested in mammalian cell culture, such as an in vitro organ culture assay, to determine whether the intended interference with expression of a targeted gene has occurred. The unique advantage of siRNA makes it possible to be combined with multiple siRNA duplexes to target multiple disease causing genes in the same treatment, since all siRNA duplexes are chemically homogenous with same source of origin and same manufacturing process.

A preferred animal wound model is a back skin excisional wound model in a Balb/c mouse or a back excisional wound model in a pig. In another aspect, the animal wound model is a skin burn wound model in a pig. In a further aspect, the animal wound model is a back skin excisional wound model in a transgenic diabetic (db+/db+) mouse. Preferably, the siRNA molecules are evaluated in at least two of the animal models. In one embodiment, the method further includes the steps of adding a pharmaceutically acceptable carrier to each of the siRNA molecules selected by step (b) to form pharmaceutical compositions and evaluating each of the pharmaceutical compositions in the animal wound model or models.

In one embodiment, the siRNA sequences are prepared in such way that each one can target and inhibit the same gene from, at least, both human and mouse, or human and non-human primate. In one aspect, the siRNA molecules bind to both a human mRNA molecule and a homologous mouse mRNA molecule. That is, the human and mouse mRNA molecules encode proteins that are substantially the same in structure or function. Therefore, the efficacy and toxicity reactions observed in the mouse disease models provide a good understanding about what is going to happen in humans. More importantly, the siRNA molecules tested in the mouse model are good candidates for human pharmaceutical agents. The human/mouse homology design of an siRNA drug agent can eliminate the toxicity and adverse effect of those species specificities observed in monoclonal antibody drugs.

In one embodiment, the invention provides a composition comprising two or more different siRNA molecules that bind to an mRNA that codes for TGFβ1 protein in a mammalian cell and two or more different siRNA molecules that bind to an mRNA that codes for COX-2 protein in a mammalian cell. The molecules may bind to different nucleotide sequences within the target mRNA. The siRNA molecules can produce additive or synergistic effects in the cells, depending on the compositions and structures of the particular molecules. In a preferred embodiment, they produce a synergistic effect. In certain applications of these embodiments, the siRNA molecules are selected from the ones identified in Table 1.

The siRNA molecules are combined with a pharmaceutically acceptable carrier to provide pharmaceutical compositions for administering to a mammal. In one aspect of this embodiment, the mammal is a laboratory animal, which includes dogs, cats, pigs, non-human primates, and rodents, such as mice, rats, and guinea pigs. In another aspect, the mammal is a human.

The carrier is a histidine-lysine copolymer that forms a nanoparticle containing an siRNA molecule, wherein the nanoparticle has a size of 100-400 nm in diameter. In one aspect of this embodiment, the carrier is selected from the group consisting of the HKP species, H3K4b and PT73, which have a Lysine backbone with four branches containing multiple repeats of Histidine, Lysine, or Asparagine. When an HKP aqueous was mixed with siRNA at a N/P ratio of 4:1 by mass, the nanoparticles (average size of 100-200 nm in diameter) were self-assembled. In another aspect of this embodiment, the HKP has the following formula: (R)K(R)—K(R)—(R)K(X), where R=KHHHKHHHKHHHKHHHK (SEQ ID NO: 5), or R=KHHHKHHHNHHHNHHH (SEQ ID NO: 6), X=C(O)NH2, K=lysine, H=histidine, and N=asparagine.

In still another aspect of this embodiment, the HKP has the following formula: (R)K(R)—K(R)—(R)K(X), where R=KHHHKHHHKHHHKHHHK (SEQ ID NO: 5), X=C(O)NH2, K=lysine, H=histidine.

The compositions of the invention are useful for downregulating pro-fibrotic factors, such as α-smooth muscle actin (α-SMA), Hydroxyproline Acid, Smad 3, and Connective Tissue Growth Factor (CTGF), and fibrotic pathways, such as TGF-β1/Smad 3/α-SMA/Collagen I-III, in the cells of a tissue of a mammal. A therapeutically effective amount of the composition is administered to the tissue of the mammal. We hypothesized that using RNAi blocking the upstream factor of the pathway, such as TGF-β1, is a more potent inhibitor. Knowing the complicated network involved in this pathway, we hypothesized that inhibition of a related factor, such as COX-2, in a different pathway may result in a synergistic effort for tighter control of the fibrosis pathway and its relevant network. In one embodiment, the tissue is skin scar, liver, lung, kidney, or heart tissue. In one aspect of this embodiment, the tissue is skin scar tissue. In another embodiment, the cells comprise fibroblasts and myofibroblasts. In one aspect of this embodiment, the fibroblasts and myofibroblasts are dermal fibroblasts and myofibroblasts. Preferably, the mammal is a human.

The compositions of the invention are also useful for activating fibroblast and myofibroblast apoptosis in the tissue of a mammal. This reduces tissue fibrosis caused by scarring after chronic inflammation of the tissue. A therapeutically effective amount of the composition is administered to the tissue of the mammal. Such apoptosis may be determined and measured by measuring the apoptotic cell population with FACS analysis, counting body numbers, and detecting expression levels of TGF-β1, COX-2, α-SMA, Collagen I and Collagen III, Hydroxyproline acid, in vitro and in vivo. In one embodiment, the tissue is skin scar, liver, lung, kidney, or heart tissue. In one aspect of this embodiment, the tissue is skin scar tissue. In another embodiment, the fibroblasts and myofibroblasts are dermal fibroblasts and myofibroblasts. Preferably, the mammal is a human.

One particular embodiment of the invention provides a method of activating fibroblast and myofibroblast apoptosis in a tissue of a human, comprising injecting into the tissue a therapeutically effective amount of a composition comprising the siRNA molecule hmTF-25-2: sense, 5'-r(CCCAAGGGCUACCAUGCCAACUUCU)-3' (SEQ ID NO: 1), antisense, 5'-r(AGAAGUUGGCAUGGUAGCCCUUGGG)-3' (SEQ ID NO: 2), the siRNA molecule hmCX-25-1: sense, 5'-r(GGUCUGGUGCCUGGUCUGAUGAUGU)-3' (SEQ ID NO: 3), antisense, 5'-r(ACAUCAUCAGACCAGGCACCAGACC)-3' (SEQ ID NO: 4), and a pharmaceutically acceptable carrier comprising a pharmaceutically acceptable histidine-lysine co-polymer. In one aspect of this embodiment, the histidine-lysine co-polymer comprises the histidine-lysine co-polymer species H3K4b or the histidine-lysine co-polymer species PT73. In another aspect of this embodiment, the histidine-lysine co-polymer has the formula (R)K(R)—K(R)—(R)K(X), where R=KHHHKHHHKHHHKHHHK (SEQ ID NO: 5), X=C(O)NH2, K=lysine, H=histidine, and N=asparagine. In still another aspect of this embodiment, the histidine-lysine co-polymer has the formula (R)K(R)—K(R)—(R)K(X), where R=KHHHKHHHKHHHKHHHK (SEQ ID NO: 5), or R=KHHHKHHHKHHHHKHHHK (SEQ ID NO: 7), X=C(O)NH2, K=lysine, H=histidine.

The compositions of the invention are also useful for reducing the size of a hypertrophic scar in the tissue of a mammal. A therapeutically effective amount of the composition is administered to the scar tissue. Such tissue includes, but is not limited to, skin, liver, lung, kidney, and heart tissue. In one embodiment, the scar comprises fibroblasts and myofibroblasts. In one aspect of this embodiment, the scar comprises dermal fibroblasts in dermal myofibroblasts. The mammal may be a laboratory animal, such as a dog, cat, pig, non-human primate, or rodent, such as a mouse, rat, or guinea pig. Preferably, the mammal is a human. In one embodiment, hypertrophic scar formation is reversed.

One particular embodiment of the invention provides a method of reducing the size of a hypertrophic scar in the skin tissue of a human, comprising injecting into the scar tissue a therapeutically effective amount of a composition comprising the siRNA molecule hmTF-25-2: sense, 5'-r(CCCAAGGGCUACCAUGCCAACUUCU)-3' (SEQ ID NO: 1), antisense, 5'-r(AGAAGUUGGCAUGGUAGCCCUUGGG)-3' (SEQ ID NO: 2), the siRNA molecule hmCX-25-1: sense, 5'-r(GGUCUGGUGCCUGGUCUGAUGAUGU)-3' (SEQ ID NO: 3), antisense, 5'-r(ACAUCAUCAGACCAGGCACCAGACC)-3' (SEQ ID NO: 4), and a pharmaceutically acceptable carrier comprising a pharmaceutically acceptable histidine-lysine co-polymer. In one aspect of this embodiment, the histidine-lysine co-polymer comprises the histidine-lysine co-polymer species H3K4b or the histidine-lysine co-polymer species PT73. In another aspect of this embodiment, the histidine-lysine co-polymer has the formula (R)K(R)—K(R)—(R)K(X), where R=KHHHKHHHKHHHKHHHK (SEQ ID NO: 5), X=C(O)NH2, K=lysine, H=histidine, and N=asparagine. In still another aspect of this embodiment, the histidine-lysine co-polymer has the formula (R)K(R)—K(R)—(R)K(X), where R=KHHHKHHHKHHHKHHHK (SEQ ID NO: 5), or R=KHHHKHHHKHHHHKHHHK (SEQ ID NO: 7), X=C(O)NH2, K=lysine, H=histidine.

The compositions of the invention are also useful for reducing fibrosis in the tissue of a mammal. A therapeutically effective amount of the composition is delivered to the tissue. Such tissue includes, but is not limited to, skin, liver, lung, kidney, and heart tissue. In one embodiment, the fibrotic tissue comprises fibroblasts and myofibroblasts. The composition may be delivered by injection into the tissue, subcutaneous injection into the mammal, or intravenous injection into the mammal. The mammal may be a laboratory animal, such as a dog, cat, pig, non-human primate, or rodent, such as a mouse, rat, or guinea pig. Preferably, the mammal is a human.

The dosages, methods of administration, and times of administration are readily determinable by a person skilled in the art, given the teachings contained herein. In one embodiment, the composition is administered by injection into the tissue. In another embodiment, the composition is ministered by subcutaneous injection into the mammal. In still another embodiment, the composition is administered intravenously to the mammal. In a preferred embodiment, the mammal is a human.

TABLE I

| | SEQ ID NO: | Sense |
|---|---|---|
| hmTF-25-1 | 8 | 5'-r(GGAUCCACGAGCCCAAGGGCUACCA)-3' |
| hmTF-25-2 | 1 | 5'-r(CCCAAGGGCUACCAUGCCAACUUCU)-3' |
| hmTF-25-3 | 9 | 5'-r(GAGCACCAUUCUCCUUGAAAGGACU)-3' |
| hmTF-25-4 | 10 | 5'-r(GAUCCACGAGCCCAAGGGCUACCAU)-3' |
| hmTF-25-5 | 11 | 5'-r(CACGAGCCCAAGGGCUACCAUGCCA)-3' |
| hmTF-25-6 | 12 | 5'-r(GAGGUCACCCGCGUGCUAAUGGUGG)-3' |
| hmTF-25-7 | 13 | 5'-r(GUACAACAGCACCCGCGACCGGGUG)-3' |
| hmTF-25-8 | 14 | 5'-r(GUGGAUCCACGAGCCCAAGGGCUAC)-3' |
| hmCX-25-1 | 3 | 5'-r(GGUCUGGUGCCUGGUCUGAUGAUGU)-3' |
| hmCX-25-2 | 15 | 5'-r(GAGCACCAUUCUCCUUGAAAGGACU)-3' |
| hmCX-25-3 | 16 | 5'-r(CCUCAAUUCAGUCUCUCAUCUGCAA)-3' |
| hmCX-25-4 | 17 | 5'-r(GAUGUUUGCAUUCUUUGCCCAGCAC)-3' |
| hmCX-25-5 | 18 | 5'-r(GUCUUUGGUCUGGUGCCUGGUCUGA)-3' |
| hmCX-25-6 | 19 | 5'-r(GUGCCUGGUCUGAUGAUGUAUGCCA)-3' |
| hmCX-25-7 | 20 | 5'-r(CACCAUUCUCCUUGAAAGGACUUAU)-3' |
| hmCX-25-8 | 21 | 5'-r(CAAUUCAGUCUCUCAUCUGCAAUAA)-3' |

| | SEQ ID NO: | Antisense |
|---|---|---|
| hmTF-25-1 | 22 | 5'-r(UGGUAGCCCUUGGGCUCGUGGAUCC)-3' |
| hmTF-25-2 | 2 | 5'-r(AGAAGUUGGCAUGGUAGCCCUUGGG)-3' |
| hmTF-25-3 | 23 | 5'-r(AGUCCUUUCAAGGAGAAUGGUGCUA)-3' |
| hmTF-25-4 | 24 | 5'-r(AUGGUAGCCCUUGGGCUCGUGGAUC)-3' |
| hmTF-25-5 | 25 | 5'-r(UGGCAUGGUAGCCCUUGGGCUCGUG)-3' |
| hmTF-25-6 | 26 | 5'-r(CCACCAUUAGCACGCGGGUGACCUC)-3' |
| hmTF-25-7 | 27 | 5'-r(CACCCGGUUGCGGGUGCUGUUGUAC)-3' |
| hmTF-25-8 | 28 | 5'-r(GUAGCCCUUGGGCUCGUGGAUCCAC)-3' |
| hmCX-25-1 | 4 | 5'-r(ACAUCAUCAGACCAGGCACCAGACC)-3' |
| hmCX-25-2 | 29 | 5'-r(AGUCCUUUCAAGGAGAAUGGUGCUC)-3' |
| hmCX-25-3 | 30 | 5'-r(UUGCAGAUGAGAGACUGAAUUGAGG)-3' |
| hmCX-25-4 | 31 | 5'-r(GUGCUGGGCAAAGAAUGCAAACAUC)-3' |
| hmCX-25-5 | 32 | 5'-r(UCAGACCAGGCACCAGACCAAAGAC)-3' |
| hmCX-25-6 | 33 | 5'-r(UGGCAUACAUCAUCAGACCAGGCAC)-3 |
| hmCX-25-7 | 34 | 5'-r(AUAAGUCCUUUCAAGGAGAAUGGUG)-3' |
| hmCX-25-8 | 35 | 5'-r(UUAUUGCAGAUGAGAGACUGAAUUG)-3' |

The following examples illustrate certain aspects of the invention and should not be construed as limiting the scope thereof.

EXAMPLES

Example 1: Simultaneous Silencing of TGF-β1 and COX-2 Gene Expressions

We first designed siRNA sequences specific to human TGF-β1 and COX-2 mRNAs in silico and then tested those sequences based on efficient cell transfection studies and analysis using qRT-PCR (FIG. 1). The potent siRNAs we selected were based on their silencing efficiencies and toxicity profiles affecting cells. When human fibroblasts isolated from the hypertrophic scar tissue were transfected with the selected siRNAs targeting either TGF-β1 or COX-2 individually or in combination, we observed an efficient siRNA entry into the cells at different stages, from initial endocytosis to endosome release of the siRNAs. The measurements of target gene silencing after the transfection indicated significant knockdown of target gene expression, with either TGF-β1$_{siRNA}$ or COX-2$_{siRNA}$ themselves, or upon combination TGF-β1/COX-2$_{siRNAs}$. Interestingly, not only was the TGF-β1$_{siRNA}$ and TGF-β1/COX-2$_{siRNAs}$ combination able to silence TGF-β1 expression, the COX-2$_{siRNA}$ was also able to down regulate TGF-β1 expression. This result implied a potential interconnection between TGF-β1 and COX-2 pathways. Similarly, TGF-β1$_{siRNA}$ was also able to silence COX-2 expression significantly. As the target genes were silenced, other pro-fibrotic factors such as α-SMA, Collagen 1 (Col1A1) and Collagen 3 (Col3A1) were also down regulated in the cell (FIG. 2). These results indicate that silencing TGF-β1 and COX-2 simultaneously in the fibroblasts has activated down regulation of multiple pro-fibrotic factors and the fibrotic pathways.

Example 2: Simultaneous Silencing of TGF-β1 and COX-2 Gene Expressions Resulted in Activation of Apoptosis of Fibroblasts/Myofibroblasts We further investigated the fate of the fibroblasts when those pro-fibrotic factors were down regulated. Electron microscope images (FIG. 3) of the fibroblast cells transfected with the either TGF-β1$_{siRNA}$ or COX-2$_{siRNA}$ only, or TGF-β1/COX-2$_{siRNAs}$ combination, illustrates that the combination treatment resulted in activation of the fibroblast apoptotic activity, but not occurred for the individual siRNA treatment group. FACS analyses of the human fibroblasts treated with the TGF-β1/COX-2$_{siRNAs}$ combination revealed a sharp increase in the apoptotic cell population (FIG. 4), compared to those treated with either TGF-β1$_{siRNA}$ or COX-2$_{siRNA}$ individually. Fibroblasts/myofibroblast treated with the TGF-β1/COX-2$_{siRNAs}$ combination showed much lower cell density and a different morphology. When we examined the expression of α-SMA protein in the human fibroblasts after the TGF-β1/COX-2$_{siRNAs}$ combination treatment, a significant reduction was observed compared to the individual siRNA treatments as measured by immunofluorescence staining (FIG. 5). We also measured the level of hydroxyproline acid (HPC) in cell culture, an indicator of the synthetic activity of ECM proteins and a hallmark of tissue fibrosis, using the human fibroblasts treated with TGF-β1/COX-2$_{siRNAs}$ combination, (FIG. 5). All above results have clearly indicated that when TGF-β1 and COX-2 gene expressions in the human fibroblasts were silenced simultaneously, a chain of down regulations of expressions of multiple fibrotic factors occurred. Consequently, the treated fibroblasts became less active and more apoptotic.

Example 3. HKP Enhances siRNA Delivery Into Human Hypertrophic Scar

To ensure efficient siRNA delivery to the hypertrophic scar, we selected a biodegradable histidine-lysine polypeptides (HKP) that has been demonstrated to provide efficient siRNA delivery in vivo (Leng et al, 2008 and Yan et al, 2008). When HKP and siRNA are mixed in aqueous solution with an optimized N/P ratio (4/1), the self-assembly of nanoparticles occurs through an electrostatic binding. These nanoparticles can be lyophilized into dry powder or formulated with aqueous solution directly (FIG. 6). The lyophilized HKP (TGF-β1/COX-2$_{siRNA}$) nanoplex powder, with an average size about 150 nm in diameter and a Zeta potential about 40 mV, is highly stable at 4° C., preserving potent activity for silencing TGF-β1 expression up to 12 months (FIG. 7).

To further understand the duration and distribution of the locally delivered siRNA, we used a human hypertrophic scar tissue implant mouse model. Two intrascar injections were conducted with one containing a naked Fluorescence-labeled FAM-siRNA and the other one containing the HKP packaged FAM-siRNA nanoparticle formulation (FIG. 8). Tissue samples were collected at 4 hours, 24 hours and 48 hours post treatment injections, and analyzed under a Fluorescence microscope. The naked siRNA are quickly dispersed after being injected into the scar tissue, and could not be detected after 24 hours. The HKP-packaged siRNA illustrated a quick dispersion and long lasting release that can be detected even after 48 hours. Therefore, we predicted that HKP-packaged siRNA nanoparticle formulation represents a useful means for evaluation of the target gene silencing in vivo. When HKP-packaged TGF-β1/COX-2$_{siRNAs}$ combination was administrated through intrascar injection, we observed a potent silencing effect at day 1, day3 and day 5 post treatment. This silencing activity resulted in parallel down regulation of both TGF-β1 and COX-2 with the greatest inhibition being seen at day 5 (FIG. 9).

Example 4. HKP-Packaged TGF-β1/COX-2siRNA Reduces Size of Human Hypertrophic Scar As expected, we first found that TGF-β1 and COX-2 are significantly over-expressed in the human hypertrophic scar (HTS) tissue from patients scar biopsy compared to the normal skin tissue (FIG. 10). Human HTS tissues were implanted onto nude mice subcutaneously for studying pathophysiology of HTS and its novel therapeutic options. After HTS tissue was implanted, we collected some of these tissues at day 7, day 14 and day 28 post implantation. We then isolated mRNA from those tissue samples for evaluating the expression dynamics of TGF-β1, COX-2 and α-SMA using qRT-PCR analyses (FIG. 11). The expression of TGF-β1 and COX-2 in the implanted human scar tissues exhibited a unique pattern with immediate escalation of TGF-β1 versus a steady increase in COX-2. The TGF-β1 expression reached a peak level at day 14 while COX-2 expression was still up regulated on day 28 post initial implantation.

The detailed procedure for HTS implant onto nude mouse back has been demonstrated by FIG. 12. The appearances of the HTS implants have been illustrated from the image of 1st week to the image of 6th month (FIG. 13). Similarly, the detailed procedure for Skin implant onto nude mouse back has also been demonstrated by FIG. 14. The appearances of the skin implants have been illustrated from the image of 1st week to the image of 6th month (FIG. 15).

Based on the readouts from FIG. 10 and FIG. 11, we decided to start the treatment of the implanted human hypertrophic scars on mice 4 weeks after surgery. A 20 μg/50 μl/cm³ HKP (TGF-β1/COX-2$_{siRNAs}$) was administered to each scar implant using 5 aliquots into 5 different sites of the scar, with three repeated injections at 5 day intervals. The HKP (TGF-β1/COX-2$_{siRNAs}$) combination treated HTS implants resulted in a significant reduction in size of implanted tissues at day 28 post-treatment (FIG. 16), about 40% in comparison to the untreated group. After taking tissue samples from those implants for further analyses, we found that not only the targeted genes TGF-β1 and COX-2 were significantly silenced based on the qRT-PCR results, but other factors such as α-SMA and col1A1 were also significantly down regulated (FIG. 17). This result provided solid evidence that the simultaneous inhibition of TGF-β1 and COX-2 contributes to the scar reduction.

Example 5. HKP (TGF-β1/COX-2$_{siRNAs}$) Reduces Size of Human Skin Grafts

Similar to human hypertrophic scar implants, human skin grafted onto the nude mouse is able to regenerate after being subjected to a full-thickness wound. This approach has been used to determine the cells involved in the connective tissue repair process following superficial wounding. In addition, this model has been used to study the wound healing process of human skin. The hypertrophic scar model is established by transplanting human skin grafts onto nude mice, resulting in obvious, persistent hypertrophic scars that have both macroscopic and histologic properties similar to human hypertrophic scars. This model makes possible the observation of the entire process of hypertrophic scar formation. Thus, it is an ideal tool for studying hypertrophic scar (Yang, et al. 2007). The initial dosing time and dosing regimen were similar to the treatment of the implanted human hypertrophic scars on mice. Four weeks after the surgery, 20 μg/50 μl/cm³ HKP (TGF-β1/COX-2$_{siRNAs}$) solution was injected into each skin graft using 5 aliquots to 5 different sites of the graft, with three repeated injections at 5 day intervals. The HKP (TGF-β1/COX-2$_{siRNAs}$) combination treated human skin grafts resulted in a significant size reduction at day 28 post-treatment (FIG. 18), about 40% in comparison to the untreated group. After taking tissue samples from those skin grafts for further analyses, we found that not only the targeted genes, TGF-β1 and COX-2, were significantly silenced based on qRT-PCR analysis but that α-SMA and col1A1 were also significantly down regulated (FIG. 19). This result is similar to what we observed with the human hypertrophic scar implants and provides further evidence that the simultaneous inhibitions of TGF-β1 and COX-2 contributes to the skin scar reduction.

Example 6. HKP (TGF-β1/COX-2siRNAs) Demonstrates a Novel Anti-Fibrotic Mechanism of Action To investigate the underlying biology of the observed scar tissue reductions with the human hypertrophic scar and human skin graft implants after HKP (TGF-β1/COX-2$_{siRNAs}$) treatment, we first measured hydroxyproline acid level from the tissue samples and then measured the differences between the treated and control groups. As we expected, the treatment groups presented a significant down regulated expression of the hydroxyproline acid, in comparison to the control groups, from both human scar and skin implants (FIG. 20). Further, using H&E, or Masson's trichrome staining, or immunohistochemistry (IHC) staining against human α-SMA, VEGF and CD3, we compared the histology between samples from both HKP (TGF-β1/COX-2$_{siRNAs}$) treated and untreated tissues. The marked differences of the tissue structures and expression levels of these pro-fibrotic factors were revealed (FIG. 21).

Example 7. HKP (TGF-β1/COX-2 siRNAs) Induced Apoptotic Activities of the Fibroblast/Myofibroblasts In Vivo We further measured the apoptotic activity of the fibroblasts in vivo as we did in the cell culture study, using a TUNEL assay. Histology images illustrated remarkably increased apoptotic fibroblasts populations in the treated tissue samples (FIG. 21). A further quantification analysis demonstrated a significant increase of the numbers of cells moving into apoptotic stage (FIG. 22).

Example 8. HKP (TGF-β1/COX-2 siRNAs) Serves as a Novel Anti-Fibrotic Therapeutic Agent The up regulation of fibroblast apoptosis in the cell culture and HTS tissue confirmed a critical role of HKP (TGF-β1/COX-2 siRNAs), in maintaining an optimized fibroblast proliferation and a balance between deposition and degradation of ECM production, to avoid fibrotic scarring. Down regulations of α-SMA, Collagen 1, Collagen 3 and hydroxproline acid in both human fibroblasts and HTS tissue after the HKP (TGF-β1/COX-$2_{siRNAs}$) treatments implicate a complex network regulating skin fibrotic scarring (FIG. 21). These results have further advanced our understanding of the mechanism of actions of the pathophysiological pathways for skin fibrotic scarring. The synergistic activity of HKP (TGF-β1/COX-$2_{siRNAs}$) silencing both TGF-β1 and COX-2 at proliferation stage and remodeling stage of skin wound healing process have provided solid evidence that the skin fibrotic scarring can be prevented and the skin hypertrophic scarring can be reversed. Therefore, we are proposing a novel siRNA based therapeutic approach of using HKP (TGF-β1/COX-2siRNAs) for hypertrophic scar treatment.

Discussion

A dermal wound healing process can be specified into three phases: inflammation, cell proliferation and matrix remodeling, which involve multiple interactions within a complex network of pro-fibrotic and anti-fibrotic molecules (Dabiri et al, 2006). After dermal injury occurs, the aggregated inflammatory cells become sources of growth factors and cytokines. When active angiogenesis and collagen synthesis ensue in concert with the tissue remodeling process, a delicate balance of deposition and degradation of fibroblast-expressed ECM determines normal skin wound healing or whether a wound heals but with HTS. Fibroblasts are the most common cells in connective tissue and key players in skin wound healing process, functioning to maintain the physical integrity of the connective tissue, participate in wound closure, and produce and remodel ECM (Wang et al, 2011). Regulation of fibroblast proliferation, their transition to myofibroblasts, and their apoptotic activity during the wound healing process can be critical modalities for therapeutic intervention.

We found that silencing TGF-β1 in human fibroblasts down regulates COX-2 expression, and vice versa (FIG. 2). Although there are reports indicating that high levels of COX-2 were able to reverse TGF-β1 into an anti-fibrotic regulator in cell culture studies, it has been suggested that these observations are due to the terminal stages of the cells used and do not reflect the early responses of TGF-β1 and COX-2 pathways to the injury in vivo (Su et al, 2010) and the evidence of up-regulated expression of these two targets in the human hypertrophic scar tissue (FIG. 9) warranted our selection of these two targets for therapeutic intervention.

We evaluated the HKP (siRNA) nanoparticle formulation, through intrascar administrations, to determine whether a clinically viable siRNA therapeutic product can be realized for treatment of the skin hypertrophic scar (Yang et al, 2007 and Rossio-Pasquier et al, 1999). We also developed scalable procedures for HKP (siRNA) nanoparticle formulation, which not only facilitated efficient siRNA delivery but exhibited no signs of adverse and toxic effects. In comparison with two ongoing clinical studies using oligo nucleotide inhibitors for the similar indications, EXC001 and RXI109, the therapeutic dose of HKP (TGF-β1/COX-$2_{siRNAs}$) formulation we used is at least 2 logs below what has been reported for 2 other agents (data not shown). We believe that the excellent potency of HKP (TGF-β1/COX-$2_{siRNAs}$) comes from not only the dual-targeted drug design but also from HKP-enhanced delivery to the site of action, which had also been demonstrated in this study (FIG. 7, 8).

The therapeutic benefits we observed through the human hypertrophic scar models further validated that simultaneous silencing of expression of two target genes indeed represents a novel treatment regimen. Using HKP-enhanced in vivo siRNA deliveries through intrascar injection, we observed significant silencing effects on TGF-β1 and COX-2 expressions about 40% (FIG. 4e, 5c), with only microgram level of the siRNA inhibitors. Further, the activation and upregulation of fibroblast apoptosis within human hypertrophic scars both in vitro (FIG. 3, 4) and in vivo (FIG. 21) after HKP (TGF-β1/COX-$2_{siRNAs}$) treatment revealed a novel underlying mechanism of action. Therefore, we hypothesized that simultaneously silencing TGF-β1 and COX-2 expression within the human hypertrophic scars is able to inhibit inflammatory activity and fibroblast proliferation, minimizing the excessive accumulation of extracellular matrix (ECM) in and around the damaged tissue. This inhibition leads to reduced ECM deposition and enhanced excessive collagen degradation. As a result, a hypertrophic scar can be reduced and eliminated eventually. Therefore, we are confident that HKP (TGF-β1/COX-$2_{siRNAs}$) will represent another clinically viable modality for novel siRNA therapeutics to reduce human skin excessive scar after damage.

The up regulation of fibroblast apoptosis in the cell culture and human HTS and skin tissue implants confirmed a critical therapeutic potential of HKP (TGF-β1/COX-$2_{siRNAs}$), in maintaining an optimized fibroblast proliferation and a balance between deposition and degradation of ECM production, to avoid fibrotic scarring. Down regulation of α-SMA, Collagen 1, Collagen 3 and hydroxproline acid in both human fibroblasts and HTS tissue, at both mRNA and protein levels after the treatments, implicates a complex network regulating skin fibrotic scarring. The results from this study have further advanced our understanding of the mechanism of actions of the pathophysiological pathways involved in the hypertrophic scar formation. The synergistic activity of HKP (TGF-β1/COX-$2_{siRNAs}$) silencing both TGF-β1 and COX-2 at the proliferation and remodeling stages of skin wound healing process provides a solid evidence that the skin hypertrophic scar formation can be potentially reversed through activation of the fibroblasts apoptosis within the scar.

Materials and Methods siRNA Sequence Design and Selection 25-mer blunt-ended siRNA duplexes targeting TGFβ1 or COX-2 mRNA sequences were designed (Table 1). (Does this refer to Table 1; i.e., should "Supplemented" be deleted?) Eight siRNA for each gene were screened in human PC3 cells for target gene silencing with qRT-PCR analyses.

Growth Inhibition In Vitro

Cells were seeded into the wells of 96-well plate at density $2 \times 10^3$ cells per well in 100 ul media. Six hours later culture media was replaced with fresh media supplemented containing Lipofectamine 2000 (Lipo2000) formulations, Lipo (TGF-β1/COX-$2_{siRNAs}$), or Lipo2000, or Lipo2000 (TGF-β$1_{siRNA}$) or Lipo2000 (COX-$2_{siRNA}$). The cells were incubated for 48 hours. For growth inhibition assay, cells were treated and analyzed with target gene silencing, FACS, α-SMA and Hydroxylproline Acid expressions.

Nanoparticle Preparation

Optimized Histidine-Lysine polymers (HKP) were applied for the siRNA delivery in vivo. One of HKP species, H3K4b, having a lysine backbone with four branches that contain multiple repeats of histidine and lysine, was used for packaging siRNAs against TGF-β1 and COX-2, with a carrier and payload ratio of 4:1 by mass. The nanoparticle (average size of 150 nm in diameter) were self-assembled.

Mouse

The 8-week old male nude mice (nu/nu Balb/c) were purchased from Center for Experimental Animals in Shanghai, China. Animal housing and experiment protocols were approved by the IACUC committee of the 9$^{th}$ People's Hospital of Shanghai.

Human Hypertrophic Scar and Skin Tissue Implant Models

Skin hypertrophic scar tissue was obtained from the surgical excisions with the informed consent were implanted under the skin on the mouse back. Scar tissue was fixed to the mouse deep fascia with 4-5 sutures before cut on skin was closed. The skin tissue samples used in experiments were from skin excisions from three women of age 23-36 undergone breast reconstruction for treatment of macromastia with signed informed consent. The skin tissues were grafted to fill the excision wounds by sutures to subcutaneous fascia and surrounding mouse skin.

Therapeutic Evaluation with the Human Tissue Implant Models

Four weeks after the human hypertrophic scar implant model established, HKP (TGF-β1/COX-2$_{siRNAs}$) was administrated via intrascar injection. The mRNA levels of TGF-β1, COX-2, α-SMA, Col1a1, and Col3a1 were analyzed with qRT-PCR. The In Situ Cell Death Detection Kit from Roche (South SF, Calif., USA) was applied for detection of apoptotic cells.

Statistical Analysis

Mean±SD was used for cell culture results, and mean±SE was used for in vivo results. An unequal variance two-tailed Student's t test was applied to compare the means of samples. A difference was considered statistically significant when P<0.05.

REFERENCES

A. J. Singer, S. S. Huang, J. S. Huang et al. A novel TGFbeta antagonist speeds reepithelialization and reduces scarring of partial thickness porcine burns. Journal of Burn Care and Research. 2009, 30, 2, 329-334.

Chen W, Fu X, Ge S, Sun T, Zhou G, Jiang D, et al. Ontogeny of expression of transforming growth factor-beta and its receptors and their possible relationship with scarless healing in human fetal skin. *Wound Repair Regen.* 2005, 13, 1:68-75.

Chia Soo, Steven R. Beanes, Fei-Ya Hu, Xinli Zhang, Catherine Dang, et al. et al. Ontogenetic Transition in Fetal Wound Transforming Growth Factor-β Regulation Correlates with Collagen Organization American Journal of Pathology. 2003, 163:2459-2476.

Dabiri. G, Campaner A, Morgan J R, Van De Water L A. TGF-beta1-dependent autocrine loop regulates the structure of focal adhesions in hypertrophic scar fibroblasts. J Invest Dermatol. 2006, 126:963-970.

E, Nedelec B, Scott P G, Ghahary A. Hypertrophic scars, keloids, and contractures. The cellular and molecular basis for therapy. Surg Clin North Am. 1997, 77, 3:701-730.

J. S. Huang, Y. H. Wang, T. Y. Ling, S. S. Chuang, F. E. Johnson, and S. S. Huang. Synthetic TGF-beta antagonist accelerates wound healing and reduces scarring. The FASEB Journal. 2002, 16, 10: 1269-1270.

Kerstin J Rolfe, Janette Richardson, Charlotte Vigor, Laurie M Irvine, Addie O Grobbelaar and Claire Linge A Role for TGFβ-1-Induced Cellular Responses during Wound Healing of the Non-Scarring Early Human Fetus? Journal of Investigative Dermatology. 2007, 127: 2656-2667.

Kopp J, Preis E, Said H, Hafemann B, Wickert L, et al. Abrogation of transforming growth factor-beta signaling by SMAD7 inhibits collagen gel contraction of human dermal fibroblasts. J Biol Chem. 2005, 280:21570-6.

Leng, Q., P Scaria, P Y Lu, Woodle M C, and A. J. Mixson. Systemic delivery of HK Raf-1siRNA Polyplexes Inhibits MDA-MB-435 Xenografts. Cancer Gene Therapy. 2008, 1-11.

Levinson H. A Paradigm of Fibroblast Activation and Dermal Wound Contraction to Guide the Development of Therapies for Chronic Wounds and Pathologic Scars. Advances In Wound Care, 2013, 2, 4:149-159. (2013).

Matsumura T, Suzuki T, Aizawa K, Sawaki D, Munemasa Y, Ishida et al. Regulation of transforming growth factor-beta-dependent cyclooxygenase-2 expression in fibroblasts. *J Biol Chem.* 2009, 284, 51:35861-71.

Matthew Rhett, Gautam S. Ghatnekar, Joseph A. Palatinus, Michael O'Quinn, Michael J. Yost and Robert G. Gourdie. Novel therapies for scar reduction and regenerative healing of skin wounds. Trends in Biotechnology, 2008, 26, 4:173-180.

McDougall S, Dalton J, Sherratt J, Maini P. Fibroblast migration and collagen deposition during dermal wound healing: mathematical modeling and clinical implications. Philos Transact A Math Phys Eng Sci, 2006, 364, 1843: 1385-1405.

Miller M C, Nanchahal J. Advances in the modulation of cutaneous wound healing and scarring. BioDrugs. 2005, 19, 6:363-381.

Mustoe T A, Cooter R D, Gold M H, Hobbs F D, Ramelet A A, et al. International clinical recommendations on scar management. Plast Reconstr Surg 2002, 110:560-571. (2002).

NCT02030275, 2014. A Study to Evaluate the Effectiveness and Safety of RXI 109 on the Outcome of Scar Revision Surgery in Healthy Adults. https://clinicaltrials.gov/ct2/results?term=RXI109

NCT01346969, 2013. Safety and Efficacy of EXC 001 in Subjects Who Have Participated in Prior Studies of EXC 001. https://clinicaltrials.gov/ct2/results?term=EXC001+AND+fibrosis Nguan Soon Tan, Liliane Michalik, Béatrice Desvergne and Walter Wahli. Genetic- or Transforming Growth Factor-β1-induced Changes in Epidermal Peroxisome Proliferator-activated Receptor β/δ Expression Dictate Wound Repair Kinetics. *The Journal of Biological Chemistry.* 2005, 280:18163-18170.

Rossio-Pasquier P[1], Casanova D, Jomard A, Démarchez M. Wound healing of human skin transplanted onto the nude mouse after a superficial excisional injury: human dermal reconstruction is achieved in several steps by two different fibroblast subpopulations. *Arch Dermatol Res.* 1999, 291, 11:591-9.

Su W H, Cheng M H, Lee W L, Tsou T S, Chang W H and Chen C S, et al. Nonsteroidal anti-inflammatory drugs for wounds: pain relief or excessive scar formation? *Mediators Inflamm.* Article ID: 413238. 2010, 1-8.

Sung I I Kim, Hee-Jun Na, Yan Ding, Zhibo Wang, Seon Jin Lee and Mary E Choi. Autophagy Promotes intracellular degradation of type I collagen induced by TGF-β1. The Jour. Of Biological Chemistry, 2012, 287, 15:11677-11687.

Tredget EWynn T A, Ramalingam T R. Mechanisms of fibrosis: therapeutic translation for fibrotic disease. *Nat Med.* 2012, 18, 7:1028-40.

V. L. Kumar and Y. M. Shivkar. Involvement of prostaglandins in inflammation induced by latex of Calotropis procera. Mediators of Inflammation. 2004, 13, 3) 151-155.

Yan, Z W, P Y Lu and LY Li et al. The Human Rhomboid Family-1 Gene RHBDF1 Is Essential to Cancer Cells Survival and Critical in EGFR Activation. Molecular Cancer Therapeutics. 2008, 7(6):1355-64.

Yang D Y, Li S R, Wu J L, Chen Y Q, Li G, Bi S, et al. Establishment of a hypertrophic scar model by transplanting full-thickness human skin grafts onto the backs of nude mice. *Plast Reconstr Surg.* 2007, 119, 1:104-9

Wilgus T A, Bergdall V K, Tober K L, Hill K J, Mitra S, Flavahan N A, et al. The impact of cyclooxygenase-2 mediated inflammation on scarless fetal wound, 2 mediated inflammation on scarless fetal wound healing. *Am J Pathol.* 2004, 165, 3:753-61.

Wang J, Ding J, Jiao H, Honardoust D, Momtazi M, Shankowsky H A, et al. Human hypertrophic scar-like nude mouse model: characterization of the molecular and cellular biology of the scar process. *Wound Repair Regen.* 2011, 19, 2:274-85.

Zhu Z, Ding J, Shankowsky H A, Tredget E E. The molecular mechanism of hypertrophic scar. *J Cell Commun Signal.* 2013, 7, 4:239-52.

The disclosures of all publications identified herein, including issued patents and published patent applications, and all database entries identified herein by url addresses or accession numbers are incorporated herein by reference in their entirety.

Although this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A method of reducing fibrosis in the tissue of a mammal, comprising administering to the tissue a therapeutically effective amount of a composition comprising an siRNA molecule that binds to an mRNA that codes for TGF-β1 protein in a mammalian cell, an siRNA molecule that binds to an mRNA that codes for COX-2 protein in a mammalian cell, and a pharmaceutically acceptable carrier comprising a pharmaceutically acceptable histidine-lysine co-polymer,
   wherein said composition comprises the siRNA molecule hmTF-25-2: sense, 5'-r(CCCAAGGGCUACCAUGC-CAACUUCU)-3' (SEQ ID NO: 1), antisense, 5'-r(AGAAGUUGGCAUGGUAGCCCUUGGG)-3' (SEQ ID NO: 2), and the siRNA molecule hmCX-25-1: sense, 5'-r(GGUCUGGUGCCUGGU-CUGAUGAUGU)-3' (SEQ ID NO: 3), antisense, 5'-r(ACAUCAUCAGACCAGGCACCAGACC)-3' (SEQ ID NO: 4).

2. The method of claim 1, wherein the tissue is selected from the group consisting of skin, liver, lung, kidney, and heart tissue.

3. The method of claim 1, wherein the composition is administered by injection into the tissue.

4. The method of claim 1, wherein the composition is administered by subcutaneous injection into the mammal.

5. The method of claim 1, wherein the composition is administered intravenously to the mammal.

6. The method of claim 1, wherein the mammal is a human.

7. The method of claim 1, wherein the pharmaceutically acceptable histidine-lysine co-polymer comprises the histidine-lysine co-polymer species H3K4b or the histidine-lysine co-polymer species PT73.

8. The method of claim 1, wherein the histidine-lysine co-polymer has the formula (R)K(R)—K(R)—(R)K(X), where R=KHHHKHHHKHHHKHHHK, or R=KHHHKHHHNHHHNHHN, X=C(O)NH2, K=lysine, H=histidine, and N=asparagine.

9. The method of claim 1, wherein the histidine-lysine co-polymer has the formula (R)K(R)—K(R)—(R)K(X), where R=KHHHKHHHKHHHKHHHK, or R=KHHHKHHHKHHHHKHHHK, X=C(O)NH2, K=lysine, and H=histidine.

10. The composition of claim 8, wherein R=KHHHKHHHKHHHKHHHK.

11. The composition of claim 9, wherein R=KHHHKHHHKHHHKHHHK.

\* \* \* \* \*